United States Patent
Natoli et al.

(10) Patent No.: US 12,037,320 B2
(45) Date of Patent: Jul. 16, 2024

(54) PRO-BENEFIT-AGENT COMPOUNDS WITH HETEROCYCLIC MOIETIES

(71) Applicant: The Procter & Gamble Company, Cincinnati, OH (US)

(72) Inventors: Sean N. Natoli, Liberty Township, OH (US); Rajan Keshav Panandiker, West Chester, OH (US); Gregory Scot Miracle, Liberty Township, OH (US); Jenna Marie Hoover, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/751,763

(22) Filed: May 24, 2022

(65) Prior Publication Data
US 2023/0002330 A1    Jan. 5, 2023

(30) Foreign Application Priority Data

May 26, 2021 (EP) .................................... 21175874

(51) Int. Cl.
 C07D 263/06 (2006.01)
 A01N 43/76 (2006.01)
 C11B 9/00 (2006.01)
(52) U.S. Cl.
 CPC ........... *C07D 263/06* (2013.01); *A01N 43/76* (2013.01); *C11B 9/0096* (2013.01)
(58) Field of Classification Search
 CPC ...... C07D 263/06; A01N 43/76; C11B 9/0096
 See application file for complete search history.

(56) References Cited

U.S. PATENT DOCUMENTS

| | | | |
|---|---|---|---|
| 5,204,023 A | 4/1993 | Behan et al. | |
| 6,861,402 B1 | 3/2005 | Miracle et al. | |
| 7,867,961 B2 | 1/2011 | Tobita | |
| 8,287,844 B2 | 10/2012 | Burgo | |
| 9,326,928 B2 | 5/2016 | Tong et al. | |
| 10,552,557 B2 | 2/2020 | Frankenbach et al. | |
| 2003/0211963 A1 | 11/2003 | Bettiol et al. | |
| 2009/0275630 A1 | 11/2009 | Provost et al. | |
| 2018/0193233 A1 | 7/2018 | Burgo | |
| 2020/0239811 A1 | 7/2020 | Burgo | |
| 2020/0368164 A1 | 11/2020 | Becker et al. | |
| 2023/0220300 A1 | 7/2023 | Natoli et al. | |
| 2023/0220304 A1 | 7/2023 | Natoli et al. | |

FOREIGN PATENT DOCUMENTS

| | | | |
|---|---|---|---|
| CN | 106436323 A | 2/2017 | |
| EP | 0206729 A2 | 12/1986 | |
| EP | 0310299 A1 | 4/1989 | |
| EP | 0392619 A2 | 10/1990 | |
| JP | 2004010553 A | 1/2004 | |
| JP | 2019150783 A | 9/2019 | |
| JP | 2020083844 A | 6/2020 | |
| WO | 200127234 A1 | 4/2001 | |
| WO | 0238120 A1 | 5/2002 | |
| WO | 03033635 A1 | 4/2003 | |
| WO | 2013150044 A2 | 10/2013 | |
| WO | 2019079313 A1 | 4/2019 | |
| WO | 2020224767 A1 | 11/2020 | |

OTHER PUBLICATIONS

Polt et al, J. Am. Chem. Soc. 1989, 111, 2622-2632.*
PCT Search Report and Written Opinion for PCT/US2022/072517 dated Jul. 29, 2022, 20 pages.
EP Search Report and Written Opinion for 21175874.3 dated Oct. 25, 2021, 15 pages.
All Office Actions; U.S. Appl. No. 17/751,755, filed May 24, 2022.
Database CA [Online] Chemical Abstracts Service, Columbus, Ohio, US; 1990, Hedegus, Louis S. et al.: "Photolytic reactions of chromium aminocarbene complexes. Conversion of amides to alpha-amino-acids", XP002804409, Journal of the American Chemical Society, vol. 112, No. 6, 1990, pp. 3.
Database CA [Online] Chemical Abstracts Service, Columbus, Ohio, US; Bezencon, Oliver et al: "Alkylations of chiral imidazolidinones derived from di- and triglycine and attempts at cyclizations to give cycloisodityrosines", XP002804411, Liebigs Annalen , (8), 1259-1276 Coden: Lanaem; ISSN: 0947-3440, 1996.
Database CA [Online] Chemical Abstracts Service, Columbus, Ohio, US; Coulton, Steven et al: "Synthesis of novel 2-oxo-4-thia-1-azabicyclo[3.3. O]oct-7-ene-8-carboxylic acid derivatives.", XP002804410, Journal of the Chemical Society, Perkin Transactions 1: Organic and Bio-Organic Chemistry, 1972-1999, pp. 4.
Database CA [Online] Chemical Abstracts Service, Columbus, Ohio, US; Gaisina, Karina R. et al: "Non-pericyclic cycloaddition of gemdifluorosubstituted azomethine ylides to the C=O bond: computational study and synthesis of fluorinated oxazole derivatives", XP002804414, Organic & Biomolecular Chemistry, 15(21 ), 4579-4586 Coden: Obcrak; ISSN: 1477-0520, 2017.
Database CA [Online] Chemical Abstracts Service, Columbus, Ohio, US; Iwanowicz, Edwin J. et al: "The enantioselective synthesis of anti-.beta.-hydroxy .alpha.-amino acids via the reaction of lithium enolates of glycine bearing an oxazolidine chiral auxiliary with aldehydes", XP002804413, SYNLETT, (6), 664-666 Coden: SYNLES; ISSN: 0936-5214, 1998.

(Continued)

*Primary Examiner* — Kamal A Saeed

(74) *Attorney, Agent, or Firm* — Andrew J. Mueller; Gregory S. Darley-Emerson

(57) ABSTRACT

Pro-benefit-agent compounds having heterocyclic moieties that include a benefit agent fragment derived from benefit agents, such as perfume raw materials, that include an aldehyde moiety or a ketone moiety. The pro-benefit-agent compounds may be derived from modified amino acids. Related treatment compositions, premix compositions, precursor compounds, and methods of making and using such materials and compositions.

10 Claims, 1 Drawing Sheet

(56) References Cited

OTHER PUBLICATIONS

Database CA [Online] Chemical Abstracts Service, Columbus, Ohio, US; Panek, James S. et al: "An Improved Synthesis of (4S,5S)-2-Phenyl-4-(methoxycarbonyl)-5- isopropyloxazoline from (S)-Phenylglycinol", XP002804412, Journal of Organic Chemistry, 63(7), 2382-2384 Coden:JOCEAH; ISSN: 0022-3263, 1998.

Database CA [Online] Chemical Abstracts Service, Columbus, Ohio, US; Polt, Robin et al: "Stereoselective alkylation of glycine units in dipeptide derivatives. "Chirality transfer" via a pivalaldehyde N,N-acetalcenter", XP002804408, Journal of the American Chemical Society, vol. 111, No. 7, 1989,—1989, pp. 4.

Kuhnt Tobias et al: "Controlled fragrance release from galactosebased pro-fragrances", RSC ADV., vol. 4, No. 92, Jan. 1, 2014 (Jan. 1, 2014), pp. 50882-50890, XP055849079.Retrieved from the Internet:URL :https ://pubs. rsc.org/en/content/articlepdf /2014/ra/ c4ra07728h.

Unpublished U.S. Appl. No. 17/751,755, filed May 24, 2022, to Sean N. Natoli et al.

Andreas Herrmann, "Controlled Release of Volatiles under Mild Reaction Conditions: From Nature to Everyday Products", vol. 46, 2007, pp. 5836-5863.

Pinazo et al. "Amino acid-based surfactants: New antimicrobial agents", Advances in Colloid and Interface Science, Dec. 15, 2015, pp. 17-39.

Pérez et al. "Gemini surfactants from natural amino acids", Advances in Colloid and Interface Science, Oct. 24, 2013, pp. 134-155.

Qing-Yi et al. "The antimicrobial activities of the cinnamaldehyde adducts with amino acids", International Journal of Food Microbiology, Aug. 4, 2011, pp. 164-170.

Tripathy et al., "Synthesis, chemistry, physicochemical properties and industrial applications of amino acid surfactants: A review", Comptes Rendus Chimie, Feb. 3, 2018, pp. 112-130.

\* cited by examiner

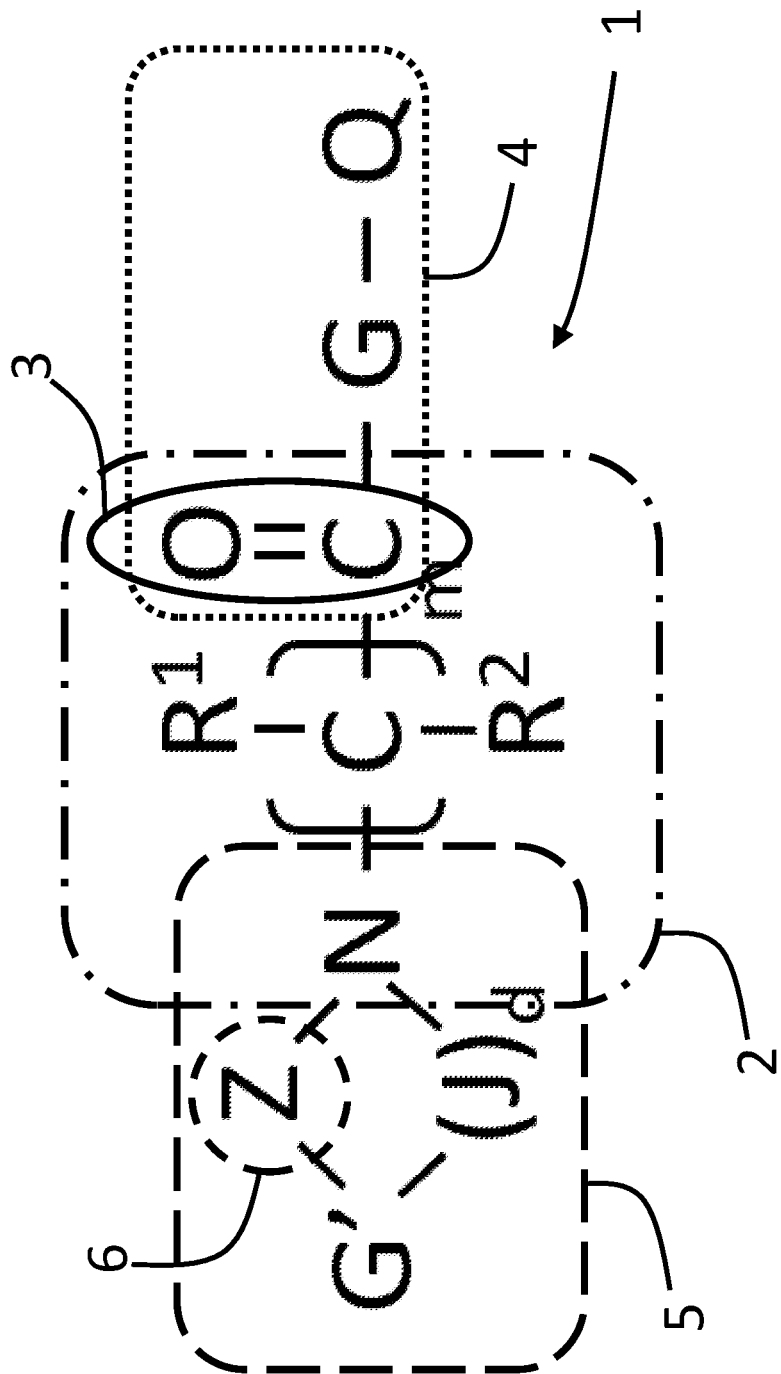

PRO-BENEFIT-AGENT COMPOUNDS WITH HETEROCYCLIC MOIETIES

FIELD OF THE INVENTION

The present disclosure relates to certain pro-benefit-agent compounds having heterocyclic moieties, related precursor compounds, related premixes, related treatment compositions, and methods of making and using such materials and compositions. The pro-benefit-agent compounds may be derived from hydrophobically-modified amino acids.

BACKGROUND OF THE INVENTION

Manufacturers of treatment compositions are continuously seeking ways to improve the delivery efficiency and/or performance benefits associated with certain benefit agents. The use of pro-benefit-agent compounds, in which a benefit agent fragment is joined by a cleavable or hydrolysable bond to a carrier molecule and then released when the bond breaks, can be a useful strategy. For example, certain amine compounds may be the basis of pro-perfume or pro-fragrance technologies. However, there remains room for improvement with regard to stability and/or deposition profiles. An additional area of need is the development of pro-perfumes that are substantially free of color forming moieties when combined with benefit agents that have conjugated π-systems.

Furthermore, consumers may desire materials that are associated with desirable environmental or sustainability profiles.

There is a need for pro-benefit-agent compounds that provide improved delivery, release, and/or stability profiles, as well as treatment compositions that include such compounds. There is also a need for methods of making and using such treatment compositions.

SUMMARY OF THE INVENTION

The present disclosure relates to pro-benefit-agent compounds that include heterocyclic moieties formed, in part, from benefit agent fragments.

For example, the present disclosure relates to a pro-benefit-agent compound, where the compound includes: a carbon-containing core, the carbon-containing core including a carbon backbone, one or more side groups, a nitrogen atom, and a carbonyl group, where the carbonyl group is part of a carbonyl-containing moiety that is selected from an ester moiety, an amide moiety, or a thioester moiety, where the carbonyl-containing moiety includes a first heteroatom joined to the carbon of the carbonyl group, where the first heteroatom is selected from oxygen, nitrogen, or sulfur, where the carbonyl-containing moiety further includes a first monovalent moiety joined to the first heteroatom, where the first monovalent moiety is an organic group that includes from 1 to 34 chain atoms; and a benefit agent fragment, where a carbon atom of the benefit agent fragment, the nitrogen of the carbon-containing core, and a second heteroatom are part of a heterocyclic moiety, where the second heteroatom is selected from oxygen, nitrogen, and sulfur, where the second heteroatom is not part of a side group of the core, wherein the carbon atom of the benefit agent fragment is bonded to the nitrogen and the second heteroatom, and where the benefit agent fragment is derived from a benefit agent, the benefit agent including an aldehyde moiety, a ketone moiety, or combinations thereof, where the heterocyclic moiety optionally further includes a second monovalent moiety that is an organic group comprising from 1 to 34 chain atoms, preferably carbon atoms; where at least one of the following is true: (a) at least one of the first monovalent moiety and the second monovalent moiety, if present, includes at least five, preferably at least eight, chain atoms, preferably carbon atoms, and/or (b) the second monovalent moiety is present, and the sum of the number of chain atoms, preferably carbon chain atoms, in the first monovalent moiety and the second monovalent moiety is at least eight.

The pro-benefit-agent compound is preferably derived from a modified amino acid.

The present disclosure also relates to treatment compositions that include an adjunct ingredient and a pro-benefit-agent compound as described above.

The present disclosure also relates to pro-benefit-agent precursor compounds. The precursor compound may be characterized by the following structure:

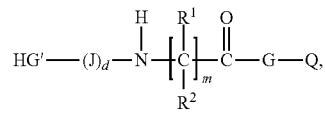

where the groups and indices are as described in the present disclosure.

The present disclosure also relates to a premix composition that includes: a pro-benefit-agent precursor compound as described above, and a benefit agent, where the benefit agent includes an aldehyde moiety, a ketone moiety, or combinations thereof. The pro-benefit-agent precursor compound and the benefit agent may optionally react to form a pro-benefit agent compound as described herein. In the premix compositions, the sum of the weight percents of the pro-benefit-agent precursor compound, the benefit agent, and the pro-benefit-agent compound, if present, may be from about 10% to about 100%, preferably from about 25% to about 100%, more preferably from about 50% to about 100%, even more preferably from about 75% to about 100%, by weight of the premix composition.

The present disclosure also relates to methods of making treatment compositions as described above. The method may include at least one of the following: (a) combining a pro-benefit-agent compound with an adjunct ingredient, preferably wherein the adjunct ingredient is part of a base composition; (b) combining a premix composition as described above with an adjunct ingredient, preferably where the adjunct ingredient is part of a base composition; (c) combining a pro-benefit-agent precursor compound, a benefit agent, and an adjunct ingredient, preferably wherein the adjunct ingredient is part of a base composition and the pro-benefit-agent precursor compound and the benefit agent are each added to the base composition as separate inputs.

The present disclosure also relates to methods of treating an article or a surface, where the method comprises treating the article or surface with a treatment composition according to the present disclosure, optionally in the presence of water.

BRIEF DESCRIPTION OF THE DRAWINGS

The FIGURES herein are illustrative in nature and are not intended to be limiting.

FIG. 1 shows an annotated structure of an exemplary pro-benefit-agent compound according to the present disclosure, for example according to Formula II.

DETAILED DESCRIPTION OF THE INVENTION

The present disclosure relates to pro-benefit-agent compounds, which may be derived from modified amino acids. The compounds may include a fragment or residue of a benefit agent, such as a perfume raw material or an antimicrobial agent, that includes an aldehyde or ketone moiety. In the pro-benefit-agent compounds of the present disclosure, the benefit agent fragment or residue is joined to the nitrogen atom of the modified amino acid and another heteroatom to form a heterocyclic moiety with other atoms. Without wishing to be bound by theory, it is believed that when the bonds that link the benefit agent fragment to the nitrogen atom and the second heteroatom are cleaved, the benefit agent is released. In addition to providing a beneficial release profile, it is believed that the character of the heterocyclic moiety tends provide improved stability, particularly improved color stability, in treatment compositions comprising such compounds, compared to other nitrogen-containing pro-benefit-agent compounds.

Furthermore, the modified amino acid comprises one or more monovalent moieties that are organic groups that increase the relative hydrophobicity of the compound. For example, a first monovalent organic moiety may be attached to the acid end of the amino acid, thereby forming a carbonyl-containing group, which may be selected from an ester group, an amide group, or a thioester group. Additionally or alternatively, separate from any organic moieties that form a portion of the benefit agent fragment, a second monovalent organic group may be attached to the heterocyclic moiety. It is believed that the hydrophobic character imparted by the organic group(s) improve the delivery and/or deposition of the pro-benefit-agent compound to an intended target surface or article.

Such pro-benefit-agent compounds, related treatment compositions, and related methods are described in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein the phrase "fabric care composition" includes compositions and formulations designed for treating fabric. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, detergent contained on or in a porous substrate or nonwoven sheet, and other suitable forms that may be apparent to one skilled in the art in view of the teachings herein. Such compositions may be used as a pre-laundering treatment, a post-laundering treatment, or may be added during the rinse or wash cycle of the laundering operation.

As used herein, the phrase "chain atoms" means the sum of all atoms in an indicated group or moiety, excluding hydrogen atoms. The chain atoms may be in a linear configuration, a branched configuration, and/or a ring configuration.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Pro-Benefit-Agent Compounds

The present disclosure relates to pro-benefit-agent compounds. The pro-benefit-agent compounds include a fragment (for example, a residue) of a benefit agent. The benefit agent from which the fragment is derived comprises an oxygen-containing moiety, namely an aldehyde moiety or a ketone moiety.

The benefit agent fragment, which may be a first benefit agent fragment, is attached to a nitrogen atom of a carrier molecule by a carbon/nitrogen linking bond. As described in more detail below, the benefit agent is also attached to another heteroatom. The nitrogen, a carbon of the benefit agent fragment, and the second heteroatom form a portion of a heterocyclic moiety.

When the bonds that join the benefit agent fragment to the heterocyclic are cleaved, the benefit agent is released. The release of the benefit agent may be triggered by any suitable mechanism, such as the presence of water or heat, preferably water, particularly when the linking bond is, for example, a N—C—O bond.

The pro-benefit-agent compounds of the present disclosure may be derived from amino acids that have been modified. Proteinogenic amino acids may be a preferred starting material, as such compounds are attractive for environmental or sustainability reasons, as they tend to be naturally occurring. For most naturally-occurring amino acids, the stereogenic carbon alpha to the amino group has the L-configuration. D-Amino acids are occasionally found in nature. While either L- or D-Amino acids as well as mixtures may be used, economic factors may lead to a preference for the more abundant L-Amino acids. Relatedly, biosynthesized amino acids may be preferred.

The starting amino acids may be modified by reacting the carboxylic acid group of the amino acid (a) with an alcohol of an organic group via an esterification reaction, (b) with an amine of an organic group via an amidation reaction, or (c) with a thiol group of an organic group via a thioesterification reaction. Such reactions can result in ester, amide, or thioester linking groups, respectively. Such linking groups, each of which is a type of carbonyl-containing moiety group, may be preferred compared to others for ease of reaction. Compounds formed with such carbonyl-containing moieties may even be preferred for environmental reasons, as these types of groups may break (e.g., hydrolyze) over time and/or in the presence of water, leaving the core material to revert, for example, to a common amino acid.

The present disclosure relates to a pro-benefit-agent compound, where the compound comprises: a carbon-containing core, the core comprising a carbon backbone, one or more side groups, a nitrogen atom, and a carbonyl group, wherein the carbonyl group is part of a carbonyl-containing moiety that is selected from an ester moiety, an amide moiety, or a thioester moiety, wherein the carbonyl-containing moiety comprises a first heteroatom joined to the carbon of the carbonyl group, wherein the first heteroatom is selected from oxygen, nitrogen, or sulfur, wherein the carbonyl-containing moiety further comprises a first monovalent moiety joined to the first heteroatom, wherein the first monovalent moiety is an organic group comprising from 1 to 34 chain atoms; a benefit agent fragment, wherein a carbon atom of the benefit agent fragment, the nitrogen of the carbon-containing core, and a second heteroatom are part of a heterocyclic moiety, wherein the second heteroatom is selected from oxygen, nitrogen, and sulfur, wherein the second heteroatom is not part of a side group of the core, wherein the carbon atom of the benefit agent fragment is bonded to the nitrogen and the second heteroatom, and wherein the benefit agent fragment is derived from a benefit agent, the benefit agent comprising an aldehyde moiety, a ketone moiety, or combinations thereof, wherein the heterocyclic moiety optionally comprises a second monovalent moiety (not bound directly to the carbon atom of the benefit agent) that is an organic group comprising from 1 to 34 chain atoms, preferably carbon atoms, wherein at least one of the following is true: (a) at least one of the first monovalent moiety and the second monovalent moiety, if present, comprises at least five, preferably at least eight, chain atoms, preferably carbon atoms, and/or (b) the second monovalent moiety is present, and the sum of the number of chain atoms, preferably carbon chain atoms, in the first monovalent moiety and the second monovalent moiety is at least eight.

The carbon-containing core comprises a carbon backbone. The carbon backbone is understood to not include the carbons of the carbonyl-containing moiety or the side group(s), if any. The carbon backbone may comprise from one to six carbon atoms, preferably from one to three carbon atoms, more preferably one carbon atom. Relatively fewer carbon atoms may be preferred for mass-efficiency reasons. In particular, backbones comprising only one carbon atom may be preferred because such structures are indicative of naturally-occurring, proteinogenic amino acids.

The carbon-containing core may be derived from an amino acid. Preferably, the core is derived from a proteinogenic amino acid. In particular, naturally-derived or biosynthesized amino acids may be preferred. Such materials may be preferred for environmental/sustainability reasons, and because they tend to be readily available at reasonable costs.

The at least one side group may be selected from a hydrogen or a suitable organic group, preferably hydrogen or an organic group having from one to about twenty chain atoms, preferably carbon atoms. The at least one side group may comprise one or more functional groups, such as carboxyl groups, amine groups, thiol groups, or hydroxyl groups. The at least one side group may be linear or branched. The at least one side group may comprise an aryl ring. The compound preferably may comprise only one non-hydrogen side group (e.g., only one organic group). The compound may comprise more than one non-hydrogen side group. The at least one side group preferably comprises the side group of a proteinogenic amino acid. The carbon-containing core may comprise at least one side group that is a hydrogen, and at least one side group that is an organic group. All of the side groups may be hydrogen, for example when the core is based on or otherwise derived from glycine.

The side group may have the structure of a side group of a proteinogenic amino acid or a derivative thereof, preferably the side group of a proteinogenic amino acid selected from the group consisting of alanine, glycine, valine, phenylalanine, leucine, isoleucine, a derivative thereof, or combinations thereof, more preferably alanine, glycine, valine, phenylalanine, a derivative thereof, or combinations thereof, even more preferably alanine, glycine, a derivative thereof, or combinations thereof. Derivatives thereof may include substitutions, including benefit agent fragments being bonded to the side group derivative.

The at least one side group may comprise a member having a structure selected from the following group, where "#" represents where the side group is attached to a carbon atom of the carbon-containing core:

| Structure | Description of Structure |
|---|---|
| #—CH₃ | Side group of alanine |
| #—H | Side group of glycine |
| 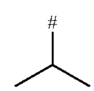 | Side group of valine |
| 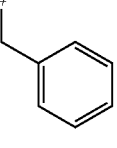 | Side group of phenylalanine |
| 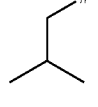 | Side group of leucine |
| 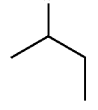 | Side group of isoleucine |

When the carbon-containing core comprises a side group having a structure that is the side group of a proteinogenic acid, preferably a side group selected from the table above, it may be preferred that the remaining side groups are hydrogen.

It may be preferred that the carbon-containing core (e.g., the parent amino acid) contains a relatively hydrophobic side group, for example those that do not contain a hydrophilic functional group, such as a carboxy group. It is believed that relatively hydrophobic side groups facilitate deposition of the pro-benefit-agent compound onto a target surface, particularly when the compound is delivered in an aqueous solution, such as a laundry wash liquor.

The proteinogenic amino acid from which the carbon-containing core is derived may be selected from the group consisting of alanine, glycine, valine, phenylalanine, leucine, isoleucine, or combinations thereof, more preferably alanine, glycine, valine, phenylalanine, or combinations thereof, even more preferably alanine, glycine, or combinations thereof. It has been found that such pro-benefit-agent compounds derived from these amino acids are particularly effective at delivering the benefit agent, particularly perfume raw materials, more particularly in laundry applications.

The pro-benefit-agent compounds of the present disclosure comprise a first monovalent moiety that is joined to the core at the carbonyl-containing moiety. The first monovalent moiety is an organic group comprising from 1 to 34 chain atoms, preferably carbon chain atoms.

The pro-benefit-agent compounds of the present disclosure may optionally comprise a second monovalent moiety that is part of the heterocyclic moiety. As used herein, the second monovalent moiety is understood to not be a part of the benefit agent fragment and/or is not bound directly to the carbon atom of the benefit agent. The second monovalent moiety may be an organic group that comprises from 1 to 34 chain atoms, preferably carbon atoms.

Without wishing to be bound by theory, it is believed that by modifying the carbon-containing core with a first and optionally a second monovalent moiety as described above, the resulting compound will be relatively hydrophobic compare to a delivery compound having an unmodified core, which facilitates deposition and/or performance benefits of the resulting pro-benefit-agent compound. Therefore, it may be important to select suitable monovalent moieties so that the desired degree of hydrophobicity is imparted to the compound.

For example, with regard to the pro-benefit-agent compounds of the present disclosure, at least one of the following may be true: (a) at least one of the first monovalent moiety and the second monovalent moiety, if present, comprises at least five, preferably at least eight, chain atoms, preferably carbon atoms, and/or (b) the second monovalent moiety is present, and the sum of the number of chain atoms, preferably carbon chain atoms, in the first monovalent moiety and the second monovalent moiety is at least eight.

It may be that the first and/or the second monovalent moiety may be relatively hydrophobic, in which case it may be referred to as a "hydrophobe." As used in this context, "hydrophobic" is meant to describe an organic group having a log P of at least 1.3, where the log P is determined for the parent alcohol of the organic group, regardless of whether the organic group is derived from an alcohol, an amine, a thiol, or an oxirane. For example, if the first monovalent moiety is a hydrophobe that is a linear group having eight carbons and is attached to the first heteroatom of the carbonyl-containing moiety at a terminal position of the hydrophobe, the log P is determined according to the log P value for 1-Octanol (in this case, log P=approx. 3.0), regardless of whether the hydrophobic group is joined to the core via an ester bond, an amide bond, or a thioester bond (see table A below). The hydrophobic moiety may be characterized by a log P of at least 1.3, or from about 2.8 to about 10.8, or from about 3.0 to about 7.8, or from about 5.0 to about 6.9. The method for determining log P is found in the Test Methods section below.

TABLE A

Calculated[a] LogP values of potential hydrophobes

| Compound Name | Smiles Code | Calculated[a] LogP Value |
|---|---|---|
| 1-Hexanol | CCCCCCO | 1.916 |
| 1-Octanol | CCCCCCCCO | 2.992 |
| 1-Decanol | CCCCCCCCCCO | 4.329 |
| 1-Dodecanol | CCCCCCCCCCCCO | 5.0 |
| 1-Tetradecanol | CCCCCCCCCCCCCCO | 6.206 |
| 1-Hexadecanol | CCCCCCCCCCCCCCCCO | 6.889 |
| 1-Octadecanol | CCCCCCCCCCCCCCCCCCO | 7.781 |

[a]The logP of an individual material is determined using the Consensus logP Computational Model, version 14.5 (Linux) available from Advanced Chemistry Development Inc. (ACD/Labs) (Toronto, Canada).

As described above, the first monovalent moiety can be joined to the carbon-containing core by a carbonyl-containing moiety that is selected from an ester moiety, an amide moiety, or a thioester moiety. Such carbonyl-containing moieties may be formed by reacting the carboxylic acid end of the core amino acid with an appropriate functional group (e.g., an alcohol, an amine, or a thiol) of a suitable organic group. It may be preferred that the carbonyl-containing moiety that joins the first monovalent moiety to the core is an ester moiety, for example due to the low cost of alcohol precursors or for the advantageous environmental profile of the resulting ester.

As described above, it is believed that a certain minimum of chain atoms, preferably carbon chain atoms, is useful for increasing the relative hydrophobicity of the group, and thus the resulting compound, which in turn can help to facilitate increased deposition or performance. The first and/or second monovalent moiety may be an organic group comprising from about 8 to about 18 chain atoms, more preferably from about 8 to about 14 chain atoms, even more preferably where most or even all of the chain atoms are carbon atoms.

When the benefit agent fragment is derived from a perfume raw material, relatively greater hydrophobicity may be preferred for deposition or performance reasons; for example, when the benefit agent to be released is a perfume raw material, at least one of the first monovalent moiety and the second monovalent moiety may be an organic group comprising from about 8 to about 18, preferably from about 10 to about 18, more preferably from about 12 to about 18, even more preferably from about 12 to about 16 chain atoms, preferably where most or even all of the chain atoms are carbon atoms.

When the benefit agent fragment is a derived from an antimicrobial agent, relatively less hydrophobicity may be preferred for performance reasons; for example, when the benefit agent to be released is an antimicrobial agent, the organic group may comprise from about 6 to about 14, preferably from about 6 to about 12, preferably from about 8 to about 12, preferably more preferably from about 8 to about 10 chain atoms, preferably where the chain atoms are carbon atoms.

The hydrophobic moiety may be optionally substituted, although it is preferred that such substitutions are selected so as to maintain the hydrophobic character of the organic group. For example, the organic group may comprise relatively hydrophobic substitutions. Additionally or alternatively, the organic group may comprise hydrophilic substitutions, but it is preferred that they are kept to a minimum and/or that the number of chain atoms is selected accordingly to counteract some of the hydrophilicity of the substitution. For example, if the organic group comprises a hydroxyl substitution, it may be preferred that the organic group comprises at least 10, preferably at least 12, carbon atoms.

The first and/or second monovalent moiety may be an unsubstituted organic group, an unbranched organic group, or a combination thereof. Preferably, the first and/or second monovalent moiety is both unsubstituted and unbranched. Such moieties may be preferred because of convenient availability, performance profiles, and relatively low environmental impact. Suitable moieties may be derived from n-Octanol, n-Decanol, n-Dodecanol, and the like.

The first and/or second monovalent moieties may be derived from a mixture of feedstock materials, such as fatty alcohols. The feedstock materials may include materials having variable chain lengths. In such cases, the chain lengths described herein for the first and second moieties are understood to be weight average chain lengths.

Additionally or alternatively, the feedstock materials may include some materials that are linear and some materials that are branched. Therefore, when the feedstocks are reacted to form the precursors or pro-benefit-agent compounds of the present disclosure, some materials will include linear monovalent moieties and others will include branched monovalent moieties. Such mixtures are contemplated in the present disclosure.

The first and/or second monovalent moiety may comprise a second fragment of a second benefit agent, which may ultimately be released from the pro-benefit-agent compound in addition to the benefit agent that is joined as a fragment to the nitrogen atom and second heteroatom of the heterocycle, which may be called a first benefit agent. Such configurations may be preferred for loading efficiency reasons; two fragments may be joined to, and released from, the compound. Such configurations may also be preferred to allow for a variety of benefit agents to be released from the same compound.

For example, the second benefit agent fragment may have a different identity than the benefit agent fragment (e.g., the first benefit agent fragment) that is part of the heterocyclic moiety. Both fragments may be in the same category of benefit agents (e.g., both are derived from perfume raw materials), but they may have different identities. Preferably, the first and second benefit agents include different functional groups. For example, the first benefit agent may comprise an aldehyde or ketone moiety, and the second benefit agent may comprise a functional group that is not an aldehyde or ketone moiety. The second benefit agent may comprise a functional group that is an alcohol, an amine, a thiol, or a combination thereof.

Preferably, the second benefit agent comprises a functional group that is an alcohol group. Such alcohol-containing materials may be preferred for ease of reaction with the carboxylic acid of the amino acid core (e.g., thereby forming an ester). Such materials may also be preferred to provide a broader spectrum of materials released from the pro-benefit-agent compound (e.g., an aldehyde- or ketone-containing benefit agent, in combination with an alcohol-containing benefit agent).

The first and/or second monovalent moiety may be substituted with a fragment of the second benefit agent. The first and/or second monovalent moiety may be (in its entirety) a fragment of the second benefit agent.

The second benefit agent may be a perfume raw material, preferably an alcohol-containing perfume raw material. In such cases, it is preferred that the first benefit agent (e.g., the parent material of the fragment attached to the nitrogen atom of the core) is also a perfume raw material, which will allow for more efficient perfume delivery and/or a more complex olfactory experience.

For environmental reasons, it may be preferred that the first and/or second monovalent moiety is derived from a naturally-derived material or feedstock, particularly when the carbon-containing core is derived from a naturally-occurring amino acid. Suitable naturally-derived materials or feedstocks may include natural fats and/or oils.

The pro-benefit-agent compound may be characterized by a structure according to Formula I:

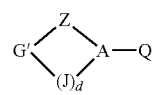

Formula I wherein Z is the benefit agent fragment, preferably a first benefit agent fragment; G' represents the second heteroatom; J represents other moieties that are part of the heterocyclic moiety and may optionally comprise a second monovalent moiety; index d is selected from 1 to 3, preferably d is from 2 to 3, more preferably d is 2; A represents the carbon-containing core (e.g., derived from a parent amino acid), where the Z and a J group are both attached to the same nitrogen atom of the A group; and Q represents the first monovalent moiety.

The pro-benefit-agent compound may be characterized by a structure according to Formula II:

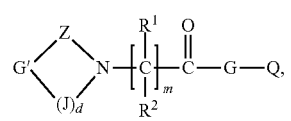

Formula II wherein the index m is selected from 1 to 6, preferably m is 1 or 2, more preferably m is 1; wherein the index d is selected from 1 to 3, preferably d is from 2 to 3, more preferably d is 2; wherein G and G' are each independently selected from —O—, —S—, or —N($R^3$)—, preferably wherein G is —O—, more preferably wherein G and G' are both —O—, wherein $R^3$, if present, is selected from —H or a monovalent moiety with a molecular weight of from about 15 to about 142 Da, preferably wherein $R^3$ is selected from —H or a monovalent moiety with a molecular weight from about 15 to about 30 Da, more preferably wherein $R^3$ is —H; wherein Q comprises from 1 to 34 chain atoms, preferably from about 1 to about 18 chain atoms, more preferably from about 2 to about 14 chain atoms, most preferably wherein the chain atoms are carbon atoms; wherein $R^1$ and $R^2$ are independently selected from —H or a monovalent moiety with a molecular weight of from about 15 to about 1000 Da, preferably independently selected from —H or a monovalent moiety with a molecular weight of from about 15 to about 507 Da, more preferably independently selected from —H or a monovalent moiety with a molecular weight of from about 15 to about 142 Da; wherein Z is the benefit agent fragment; wherein each J is independently selected from the group consisting of C($R^6$)$_2$, —O—, and —N($R^6$)—, wherein each $R^6$ is independently selected from H or a monovalent moiety with a molecular weight between 14 and 990 Da, more preferably $R^6$ is selected from H or a monovalent moiety with a molecular weight between 14 and 186 Da, even more preferably $R^6$ is H, with the proviso that a first $R^6$ and a second $R^6$ can optionally be taken together, where feasible, as a divalent substituent, preferably where the divalent substituent is selected from the group consisting of a fused ring, a spirocyclic ring, an unsaturated substituent, $=N(R^3)$, $=O$, and $=S$, wherein $R^3$ is as defined above; and wherein at least one of the following is true: (a) at least one of Q and an $R^6$, if present, comprises at least five, preferably at least eight, chain atoms, preferably carbon atoms, and/or (b) an $R^6$ is present, and the sum of the number of chain atoms, preferably carbon chain atoms, in Q and the $R^6$ is at least eight. It may be preferred that they heterocyclic ring is free of an $=O$ moiety (e.g., where the divalent substituent, if present, is not $=O$), as such moieties can slow the release of the benefit agents and/or undesirably affect the hydrophobicity of the pro-benefit agent compound, which may affect deposition efficiency.

To illustrate the above, FIG. 1 shows an annotated structure of a pro-benefit-agent compound according to the present disclosure, for example a compound according to Formula II. The pro-benefit-agent compound 1 includes a carbon-containing core 2. The core 2 includes one or more carbon atoms (depending on the value of index m) that are attached to side groups R' and $R^2$; these carbon atom(s) (not including $R^1$ or $R^2$) form(s) the carbon backbone of the compound 1. The core 2 also includes a carbonyl group 3. The carbonyl group 3 is part of a carbonyl-containing moiety 4, which may be an ester, an amide, or a thioester, depending on which type of first heteroatom (-G-) is present and is attached to -Q, the first monovalent moiety. The compound 1 also includes a heterocyclic moiety 5 that includes, in part, a benefit agent fragment 6. Although not expressly shown in FIG. 1, the compound 1 may include a second monovalent moiety joined to the heterocyclic moiety 5; the second monovalent moiety would typically be joined to a -J- group.

In Formula II, G and G' may be selected from —O—, —S—, or —N(R$^3$)—, and preferably G is —O—. The resulting ester when G is —O— may be preferred for environmental reasons, as well as convenient availability of alcohol-based feedstock materials. For clarity, the —C(O)G- moiety of Formula II represents the carbonyl-containing moiety of the carbon-containing core that is bonded to the first monovalent moiety (Q). G' may preferably be —O—, also for convenient availability and reactivity of feedstock materials, such as oxiranes.

In Formula II, G and/or G' may be selected from —N(R$^3$)—, wherein $R^3$ is selected from —H or a monovalent moiety with a molecular weight of from about 15 to about 142 Da, preferably wherein $R^3$ is selected from —H or a monovalent moiety with a molecular weight from about 15 to about 30 Da, more preferably wherein $R^3$ is —H. Relatively smaller $R^3$ moieties, and especially hydrogen, may be preferred when forming the amide bond, for example due to convenient reactions and availability of feedstock materials.

In Formula I or II, Q may comprise from 1 to 34 chain atoms, preferably from about 1 to about 18 chain atoms, more preferably from about 2 to about 12 chain atoms, most preferably wherein most or preferably even all of the chain atoms are carbon atoms. The Q group may be unsubstituted, unbranched, or a combination thereof, preferably a combination thereof.

When an $R^6$ group is present as a part of a J moiety, the $R^6$ group may be an organic group that serves as the second monovalent moiety that is part of the heterocyclic moiety. The $R^6$ group may be an organic group comprising from 1 to 34 chain atoms, preferably most or even all carbon atoms.

As described above, it is preferred that the first monovalent moiety (e.g., Q) and optionally the second monovalent moiety (e.g., $R^6$), if present, are selected so as to provide sufficient hydrophobicity for efficient deposition and/or performance benefits. At least one of the following may be true: (a) at least one of Q and an $R^6$, if present, comprises at least five, preferably at least eight, more preferably at least ten, even more preferably at least twelve, chain atoms, preferably carbon atoms, and/or (b) an $R^6$ is present, and the sum of the number of chain atoms, preferably carbon chain atoms, in Q and the $R^6$ is at least eight, preferably at least ten, more preferably at least twelve.

So long as sufficient hydrophobicity is provided, the Q group and/or the $R^6$ group may be substituted, for example with oxygen. For example, the Q group and/or the $R^6$ group may comprise an ether moiety, a hydroxyl moiety, or combinations thereof.

For example, the Q group (e.g., the first monovalent moiety) and/or an $R^6$ group (e.g., the second monovalent moiety), preferably the Q group, may comprise one or more alkoxy group, preferably selected from ethoxy, propoxy, or butoxy groups, or a combination thereof. For example, the Q group and/or the $R^6$ group may have the empirical formula of —$(C_nH_{2n}O_y)_xH$, wherein each index x is independently selected from 1 to 12, preferably x is from 4 to 10, more preferably x is from 5 to 7; wherein each index n is independently selected from 1 to 4, preferable n is 1 or 2; wherein each index y is from 0 to 1, preferably y is 1 when the group comprises alkoxy groups.

The Q group (e.g., the first monovalent moiety) and/or an $R^6$ group (e.g., the second monovalent moiety), preferably the Q group, may comprise an —OH group, particularly wherein the Q group/first monovalent moiety is derived from a diol.

For mass efficiency reasons, it may be preferred that one of Q and the $R^6$ group is relatively long while the other is relatively short. For example, Q may comprise at least 8 chain atoms, and no $R^6$ group, if present, comprises more than 4 chain atoms, preferably no $R^6$ group, if present, comprises more than 2 chain atoms, more preferably all the $R^6$ groups, if present, are hydrogens. It may be that at least one $R^6$ comprises at least 8 chain atoms, and the Q group comprises from 1 to 4 chain atoms, preferably the Q group comprises from 1 to 2 chain atoms.

The Q group may comprise a second fragment of a second benefit agent, preferably a second perfume raw material, more preferably an alcohol-containing second perfume raw material; in such cases, G may be —O—. When such materials are present, other materials may be present that comprise the carbon-containing core and the first monovalent group, but not the first benefit agent fragment that is joined to the nitrogen of the carbon-containing core.

In Formula II, $R^1$ and $R^2$ may be independently selected from —H or a monovalent moiety with a molecular weight of from about 15 to about 1000 Da, preferably independently selected from —H or a monovalent moiety with a molecular weight of from about 15 to about 507 Da, more preferably independently selected from —H or a monovalent moiety with a molecular weight of from about 15 to about 142 Da. $R^1$ and/or $R^2$ is the side group of the carbon-containing core. At least one of $R^1$ and $R^2$, preferably at least one $R^1$, is a monovalent moiety having the structure of the side chain of a proteinogenic amino acid, preferably when $R^2$ is hydrogen (—H) and m=1. It is possible for at least one of $R^1$ and $R^2$ to comprise a benefit agent fragment; such configurations may be preferred for mass efficiency reasons, in that one carrier comprises two fragments (one as part of the heterocyclic moiety, one on the side chain).

At least one $R^1$ or $R^2$ group may have the structure of the side chain of a proteinogenic amino acid, preferably the side chain of a proteinogenic amino acid selected from the group consisting of alanine, glycine, valine, phenylalanine, leucine, isoleucine, or combinations thereof, more preferably alanine, glycine, valine, phenylalanine, or combinations thereof, even more preferably alanine, glycine, or combinations thereof.

In Formula II, index m is from one to six, preferably m is from one to three, more preferably m is one. When index m is one, the carbon-containing core may be derived from a naturally-derived or biosynthesized proteinogenic amino acid, which may be preferred for environmental reasons.

In Formula I or II, the Z group represents the benefit agent fragment. Preferably, the Z moiety comprises from about 4 to about 34 carbon atoms. The Z moiety is preferably a fragment of a perfume raw material. Benefit agents and fragments thereof are discussed in more detail below.

The Z group, representing the benefit agent fragment, may be according to the following structure:

wherein "#" indicates the points of attachment to adjacent members of the heterocycle (e.g., the nitrogen atom of the core and the second heteroatom, G'), wherein $R^4$ is a monovalent organic moiety, wherein $R^5$ is —H or a monovalent organic moiety, with the proviso that $R^4$ and $R^5$ may be taken together to form a cyclic moiety. When the bonds marked by "#" are broken, the pro-benefit-agent compound releases a benefit agent according to the structure $R^5$—C(O)—$R^4$.

When the Z group is a fragment of an aldehyde-containing benefit agent, $R^5$ is a hydrogen. When the Z group is a fragment of a ketone-containing benefit agent, $R^5$ is an organic moiety. Such fragments may be derived from and/or result in the release of benefit agents according to the formula $R^4$—C(O)—$R^5$. The benefit agents, and fragments thereof, may be characterized by a relatively low molecular weight, for example from about 100 g/mol to about 1000 g/mol, preferably from about 100 g/mol to about 500 g/mol; $R^4$ and $R^5$ groups may be selected accordingly.

In Formula I, the A group may be characterized by the following structure, Formula III:

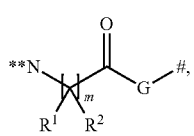

Formula III where $R^1$, $R^2$, G, m, are defined as above, where # represents the point of attachment of G to the hydrophobic group Q, and where ** represents the point of attachment to the rest of the heterocyclic moiety (e.g., to the Z group and to a J group).

The pro-benefit-agent compound may be characterized by a structure according to Formula IV:

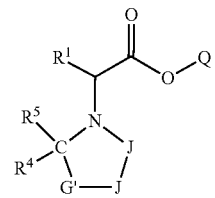

Formula IV wherein Q, $R^1$, $R^4$, and $R^5$, G', and J are as described above. Formula IV is effectively a structure according to Formula II above, where G is —O—, $R^2$ is —H, m is 1, d is 2, and Z is —C($R^4$)($R^5$)—.

In such a configuration, the pro-benefit-agent compound is believed to provide advantageous performance benefits, as well as having a beneficial environmental profile.

The pro-benefit-agent compound may be characterized by a structure according to Formula V:

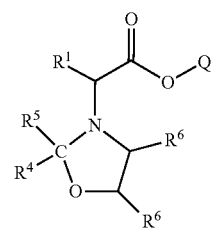

Formula V wherein Q, $R^1$, $R^4$, $R^5$, and $R^6$ are as described above. Formula V is effectively a structure according to Formula IV above, where J is —C(H)($R^6$)—, and G' is —O—. In such a configuration, the pro-benefit-agent compound is believed to provide advantageous performance benefits, as well as having a beneficial environmental profile.

The pro-benefit-agent compound may be characterized by a structure according to Formula II, where: m=1; $R^1$ is a side group of a proteinogenic amino acid; $R^2$ is —H. This embodiment may be preferred because it is can be based on a naturally-occurring amino acid core. In such cases, it may be further preferred that G═—O—, as the resulting ester may be preferred for environmental reasons.

The pro-benefit agent compound may be characterized by a structure according to Formula II, where Q is an organic group comprising from about 8 to about 18 chain atoms, preferably where most or even all the chain atoms are carbon atoms; G═—O—; m=1; $R^1$ is a side group of a proteinogenic amino acid; $R^2$ is —H; d=2; each J═C($R^6$)$_2$, preferably wherein $R^6$ is hydrogen; G'═—O—; Z is a fragment of a perfume raw material, preferably a perfume raw material that comprises an aldehyde moiety. In such a configuration, the pro-benefit-agent compound is believed to provide advantageous performance benefits, as well as having a beneficial environmental profile.

The pro-benefit agent may further comprise a second benefit agent fragment. Preferably, the pro-benefit-agent compound is characterized by a structure according to Formula II, and the second benefit agent fragment is part of a group consisting of Q, $R^1$, $R^2$, or $R^6$. Such configurations can provide efficient loading and delivery benefits.

The pro-benefit agent is preferably free of peptide bonds, as such bonds may be vulnerable to attack by protease enzymes that are present under storage, treatment, or usage conditions, such as in a treatment liquor.

The pro-benefit agent is preferably free of halogens, as such materials may limited to regulatory concerns.

Benefit Agents and Fragments Thereof

The pro-benefit-agent compounds of the present disclosure comprise benefit agent fragments that are derived from aldehyde-containing benefit agents, ketone-comprising benefit agents, or a combination thereof. The benefit agent fragment may be derived from a benefit agent that comprises an aldehyde moiety. The benefit agent fragment may be derived from a benefit agent that comprises a ketone moiety.

As used herein, the benefit agent from which the benefit agent fragment is derived may be called a parent benefit agent.

The aldehyde or ketone moiety of the parent benefit agent may react with a nitrogen atom of the compound's core (e.g., the nitrogen of an amino acid) and a second heteroatom, resulting in a carbon atom of benefit agent fragment being joined to the nitrogen atom and the second heteroatom forming part of a heterocyclic moiety (for example, N—C—O when the second heteroatom is oxygen).

It may be preferred that the parent benefit agent comprises an aldehyde moiety, as heterocyclic moieties may be conveniently formed from such agents, for example without requiring a catalyst or substantial heat energy inputs.

When the fragment's bonds to the heterocyclic moiety are broken, for example through hydrolysis, the benefit agent is released. The relevant bonds may be broken through a triggering condition, such as the presence of water or increased temperature.

The benefit agent fragment may be derived from any suitable benefit agent, which may include a perfume raw material, an antimicrobial agent, a pesticide, an insect repellant, an anti-fungal agent, a herbicidal agent, a hueing dye, an antioxidant, a non-perfume organoleptic (such as a cooling agent), or a combination thereof, preferably a perfume raw material, an antimicrobial agent, or a combination thereof, more preferably a perfume raw material. A few of these benefit agents are discussed in more detail below.

A. Perfume Raw Materials

The benefit agent may be a perfume raw material ("PRM") that comprises an aldehyde moiety, a ketone moiety, or a mixture thereof. The benefit agent fragment (e.g., the Z group) may be derived from a perfume raw material.

The term "perfume raw material" (or "PRM") as used herein refers to compounds that may have a molecular weight of at least about 100 g/mol (optionally up to about 1000 g/mol, preferably up to about 500 g/mol) and which are useful in imparting an odor, fragrance, essence, or scent, either alone or with other perfume raw materials. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994).

It may be preferred that the perfume raw material comprises an aldehyde moiety, as such materials are conveniently reacted to form a heterocyclic moiety (e.g., in the absence of a catalyst). Perfume raw materials that comprise an aldehyde moiety are provided below in Table B. It is believed that the materials provided in Table B are illustrative (but non-limiting) examples of PRMs that are suitable for use according to the present disclosure.

TABLE B

Aldehyde-containing perfume raw materials.

| Number | Registry Name | Trade Name |
|---|---|---|
| 1 | 3-Cyclohexene-1-carboxaldehyde, dimethyl- | Ligustral |
| 2 | 3-Cyclohexene-l-carboxaldehyde, 2,4,6-trimethyl- | Isocyclocitral |
| 3 | Cyclohexanemethanol, .alpha.,3,3-trimethyl-, formate | Aphermate |
| 4 | 3-(4-tert-butylphenyl)butanal; pt-bucinal; 3-(4-tert-butylphenyl)butanal | Lilial |
| 5 | 2-methylundecanal | Methyl Nonyl Acetaldehyde |
| 6 | l-methyl-3-(4-methylpent-3-enyl)cyclohex-3-ene-l-carbaldehyde; myrmac aldehyde | Precyclemone B |
| 7 | Benzenepropanal, 3-(4-ethylphenyl)-2,2-dimethylpropanal | Floralozone |
| 8 | 2,4-dimethylcyclohex-3-ene-1-carbaldehyde | Ligustral/Triplal |
| 9 | Decanal | Decyl Aldehyde |
| 10 | 10-Undecen-1-al; Undecenoic aldehyde; n-Undecenoic aldehyde; Hendecen-10-al; | Undecylenic aldehyde; Aldehyde C-11, unsaturated;Aldehyde C-11 undecylenic; |
| 11 | 8-,9 and 10-Undecenal, mixture of isomers | Intreleven aldehyde |
| 12 | Benzenepropanal, .alpha.-methyl-4-(1-methylethyl)- | Cyclamen Aldehyde |
| 13 | 2,6,10-trimethylundec-9-enal | Adoxal; Farenal |
| 14 | 4-(octahydro-4,7-methano-5H-inden-5-ylidene)butanal | Dupical |
| 15 | 3-Ethoxy-4-hydroxybenzaldehyde | Ethyl vanillin |
| 16 | tricyclo[5.2.1.02,6]decane-3-carbaldehyde | Vertral ® |
| 17 | 4,7-Methano-1H-indene-2-carboxaldehyde, octahydro-5-methoxy-; 6-Methoxy dicyclopentadiene carboxaldehyde; 8-Methoxytricyclo(5.2.2.1)decane-4-carboxaldehyde; Octahydro-5-methoxy-4,7-methano-1H-indene-2-carboxaldehyde; | Scentenal ® 981810 |

TABLE B-continued

Aldehyde-containing perfume raw materials.

| Number | Registry Name | Trade Name |
|---|---|---|
| 18 | 4-Hydroxy-3-methoxybenzaldehyde | Vanillin |
| 19 | Trans-4-decenal | Decenal-4-trans |
| 20 | α-hexyl-; α-n-Hexyl-β-phenylacrolein; 2-Hexyl-3-phenyl-2-propenal; 2-Hexyl-3-phenyl-propenal; (2Z)-2-Hexyl-3-phenyl-2-propenal; Hexyl-3-phenyl-propenal; n-Hexyl cinnamaldehyde; (2E)-2-Benzylideneoctanal; 2-[(E)-Benzylidene] octanal | α-Hexylcinnamaldehyde; α-Hexylcinnamic aldehyde; Hexyl cinnamic aldehyde; Hexylcinnamaldehyde; Cinnamaldehyde, |
| 21 | 4-Dodecenal | Tangerinal DIPG 984655 |
| 22 | 3-Cyclohexene-1-propanal,beta,4-dimethyl- | Liminal ® 955374 |
| 23 | trans-2-Dodecenal | Mandarine aldehyde 10% CITR 965765 |
| 24 | 4,8-Dimethyl-4,9-decadienal | Floral Super |
| 25 | Hydroxymyrac aldehyde; 4-(4-Hydroxy-4-methyl-pentyl)-3-cyclohexen-1-carboxyaldehyde; Lyral; Kovanol | Lyral |
| 26 | 2-Hexenal, (E)- | 2-Hexenal |
| 27 | Benzaldehyde | Benzaldehyde |
| 28 | Benzeneacetaldehyde | Phenyl Acetaldehyde |
| 29 | Benzeneacetaldehyde, .alpha.-methyl- | Hydratropic Aldehyde |
| 30 | 3-Cyclohexene-1-carboxaldehyde, 3,5-dimethyl- | Cyclal C, |
| 31 | Benzaldehyde, 4-methoxy- | Anisic Aldehyde |
| 32 | Octanal, 7-hydroxy-3,7-dimethyl- | Hydroxycitronellal |
| 33 | 3-Cyclohexene-1-carboxaldehyde, 3,6-dimethyl- | Cyclovertal |
| 34 | Octanal, 7-methoxy-3,7-dimethyl- | Methoxycitronellal Pq |
| 35 | Benzenepropanal, beta.-methyl-; 3-phenylbutanal | Trifemal |
| 36 | 4,7-Methano-1H-indenecarboxaldehyde, octahydro- | Formyltricyclodecan |
| 37 | Octanal | Octyl Aldehyde |
| 38 | 5-Heptenal, 2,6-dimethyl- | Melonal |
| 39 | Octanal, 3,7-dimethyl- | Dihydrocitronellal |
| 40 | 2-Nonenal | 2 Nonen-1-al |
| 41 | 6-Octenal, 3,7-dimethyl- | Citronellal |
| 42 | 2-Decenal | 2 Decene-1-al |
| 43 | 2,6-Octadienal, 3,7-dimethyl- | Citral |
| 44 | Undecenal | Iso C-11 Aldehyde |
| 45 | Undecanal | Undecyl Aldehyde |
| 46 | 2-Undecenal | 2-Undecene-1-Al |
| 47 | Benzaldehyde, 4-(1-methylethyl)- | Cuminic Aldehyde |
| 48 | Decanal, 2-methyl- | Methyl Octyl Acetaldehyde |
| 49 | Benzenepropanal, 4-(1,1-dimethylethyl)- | Bourgeonal |
| 50 | 2-Dodecenal | 2 Dodecene-1-al |
| 51 | Benzenepropanal, .beta.-methyl-3-(1-methylethyl)- | Florhydral |
| 52 | 1,3-Benzodioxole-5-carboxaldehyde | Heliotropin |
| 53 | 3-Cyclohexene-1-carboxaldehyde, 1-methyl-4-(4-methylpentyl)- | Vernaldehyde |
| 54 | Benzenepropanal, 4-methoxy-.alpha.-methyl- | Canthoxal |
| 55 | Cyclohexenebutanal, .alpha.,2,2,6-tetramethyl- | Cetonal |
| 56 | Dodecanal | Lauric Aldehyde |
| 57 | 5,9-Undecadienal, 2,6,10-trimethyl- | Oncidal |
| 58 | Bicyclo[2.2.2]oct-5-ene-2-carboxaldehyde, 6-methyl-8-(1-methylethyl)- | Maceal |
| 59 | 2-methyl-3-[4-(2-methylpropyl)phenyl]propanal | cyclamen homoaldehyde |
| 60 | 6-methoxy-2,6-dimethyloctanal | calypsone |
| 61 | 4-propan-2-ylbenzaldehyde | Cuminic Aldehyde |
| 62 | 3,6-dimethylcyclohex-3-ene-1-carbaldehyde | VERTOLIFF |
| 63 | 2-methyl-3-(4-methylphenyl)propanal | Jasmorange ®; satinaldehyde |
| 64 | 3-phenylprop-2-enal | Cinnamic Aldehyde |

The perfume raw material that formed the benefit agent fragment may be selected from the group consisting of the aldehyde-containing PRMs of Table A, above. The PRM that formed the PRM fragment may comprise an aldehyde moiety and preferably be selected from the group consisting of: methyl nonyl acetaldehyde: benzaldehyde; floralozone; iso-cyclocitral; triplal lilial; decyl aldehyde; undecylenic aldehyde; cyclamen (ligustral); precyclemone B; homoaldehyde; cyclamen aldehyde; dupical; oncidal; adoxal; melonal; calypsone; anisic aldehyde; heliotropin; cuminic aldehyde; scentenal; 3,6-dimethylcyclohex-3-ene-1-carbaldehyde; satinaldehyde; canthoxal; vanillin; ethyl vanillin; cinnamic aldehyde; cis-4-decenal; trans-4-decenal; cis-7-decenal; undecylenic aldehyde; trans-2-hexenal; trans-2-octenal; 2-undecenal; 2,4-dodecadeienal; cis-4-heptenal; Florydral;

butyl cinnamaldehyde; limonelal; amyl cinnamaldehyde; hexyl cinnamaldehyde; citronellal; citral; cis-3-hexen-1-al; and mixtures thereof.

As mentioned above, the pro-benefit-agent compound may include a fragment of a perfume raw material that comprises a ketone moiety. Perfume raw materials that comprise a ketone moiety are provided below in Table C. It is believed that the materials provided in Table C are illustrative (but non-limiting) examples of PRMs that are suitable for use according to the present disclosure.

TABLE C

Ketone-containing perfume raw materials

| Number | Registry Name | Trade Name |
|---|---|---|
| 1 | 2-Buten-1-one, 1-(2,6,6-trimethyl-3-cyclohexen-1-yl)- | delta-Damascone |
| 2 | (1-(2,6,6-Trimethyl-2-cyclohexen-1-yl)-2-buten-1-one); 2-Buten-1-one, 1-(2,6,6-trimethyl-2-cyclohexen-1-yl)-, (E)- | alpha-Damascone |
| 3 | (1-(2,6,6-Trimethyl-1-cyclohexen-1-yl)-2-buten-1-one); 2-Buten-1-one, 1-(2,6,6-trimethyl-1-cyclohexen-1-yl)-, (E)- | beta-Damascone |
| 4 | 2-Buten-1-one, 1-(2,6,6-trimethyl-1,3-cyclohexadien-1-yl)- | Damascenone |
| 5 | 1,1,2,3,3-pentamethyl-2,5,6,7-tetrahydroinden-4-one | Cashmeran |
| 6 | l-(5,5-dimethyl-1-cyclohexenyl)pent-4-en-1-one | Neobutenone Alpha |
| 7 | 1-(5,5-dimethyl-1-cyclohexenyl)pent-4-en-1-one | Galbascone; Dynascone |
| 8 | 1-naphthal en-2-ylethanone | Methyl Beta-Naphthyl Ketone |
| 9 | 2-(2-(4-Methy 1-3 -cy clohexen-1-yl)propyl)cyclo-pentanone | Nectary 1 |
| 10 | 2-Hexyl-2-cyclopenten-1-one (main component) | Isojasmone B 11 |
| 11 | Methyl 2,6,10-Trimethyl-2,5,9-cyclododecatrien-l-yl ketone; | Trimofix "O" |
| 12 | α-Isomethyl ionone; 5-(2,6,6-Trimethyl-2-cyclohexen-1-yl)-3-methyl-3-buten-2-one; | Methyl ionone; Methyl Ionone Alpha Iso; Methyl Ionone Gamma; Isoraldeine 70; Isoraldeine 95; Gamma Methylionone 600 UC; Alpha Daphnone; Iraldeine gamma; gamma Methyl Ionone Pure; gamma Methyl Ionone A; Gamma Methyl Ionone Coeur |
| 13 | 2-Heptylcyclopentanone; | Fleuramone; Projasmon |
| 14 | 3-(Hydroxymethyl)nonan-2-one (and isomer) | Methyl lavender ketone |
| 15 | 2-Cyclohexen-1-one, 2-methyl-5-(1-methylethenyl)-, (R)- | Laevo Carvone |
| 16 | Bicyclo[2.2. l]heptan-2-one, 1,7,7-trimethyl-, (1R)- | Camphor Gum |
| 17 | 2-Heptanone | Methyl Amyl Ketone |
| 18 | 3-Octanone | Ethyl Amyl Ketone |
| 19 | 2-Octanone | Methyl Hexyl Ketone |
| 20 | 5-Hepten-2-one, 6-methyl- | Methyl Heptenone |
| 21 | Ethanone, 1-(4-methylphenyl)- | Para Methyl Acetophenone |
| 22 | 2-Butanone, 4-phenyl- | Benzyl Acetone |
| 23 | 1,4-Methanonaphthalen-5(1H)-one, 4,4a,6,7,8,8a-hexahydro- | Tamisone |
| 24 | 2H-1-Benzopyran-2-one, 3,4-dihydro- | Dihydrocoumarin |
| 25 | Cyclohexanone, 5-methyl-2-(1-methylethyl)-, cis- | Iso Menthone |
| 26 | 2H-Pyran-2-one, 6-butyltetrahydro- | Nonalactone |
| 27 | 3-Hepten-2-one, 3,4,5,6,6-pentamethyl- | Koavone |
| 28 | Cyclopentanone, 3-methyl-2-pentyl- | Jasmylone |
| 29 | 3-Nonanone | Ethyl Hexyl Ketone |
| 30 | Ethanone, 1-(3,3-dimethylcyclohexyl)- | Herbac |
| 31 | 3-Heptanone, 5-methyl-, oxime | Stemone |
| 32 | Cyclohexanone, 2-(1-methylpropyl)- | 2-Sec-Butyl Cyclo Hexanone |
| 33 | Cyclopentanone, 2-pentyl- | Delphone |
| 34 | 2-Cyclopenten-1-one, 3-methyl-2-pentyl- | Dihydrojasmone |
| 35 | Cyclohexanone, 5-methyl-2-(l-methylethyl)-, trans- | Menthone Racemic |
| 36 | Cyclohexanone, 4-(1,1-dimethylpropyl)- | Orivone |
| 37 | 2-Undecanone | Methyl Nonyl Ketone |
| 38 | 1-Decanol | Rhodalione |
| 39 | 2-Cyclohexen-1-one, 3-methyl-5-propyl- | Livescone |
| 40 | 2-Cyclopenten-1-one, 2-methyl-3-(2-pentenyl)- | Iso Jasmone |
| 41 | Ionone | Ionone Ab |
| 42 | 3-Buten-2-one, 4-(2,6,6-trimethyl-2-cyclohexen-1-yl)-, (E)- | Ionone Alpha |

TABLE C-continued

Ketone-containing perfume raw materials

| Number | Registry Name | Trade Name |
|---|---|---|
| 43 | 3-Buten-2-one, 4-(2,6,6-trimethyl-1-cyclohexen-1-yl)- | Ionone Beta |
| 44 | 2-Buten-1-one, 1-(2,4,4-trimethyl-2-cyclohexen-1-yl)-, (E)- | Isodamascone N |
| 45 | 2H-1-Benzopyran-2-one | Coumarin |
| 46 | Cyclopentanone, 2-heptyl- | Fleur amone |
| 47 | 3-Decanone, 1-hydroxy- | Methyl Lavender Ketone |
| 48 | 1-Propanone, 1-[2-methyl-5-(1-methylethyl)-2-cyclohexen-1-yl]- | Nerone |
| 49 | 9-Undecen-2-one, 6,10-dimethyl- | Tetra Hydro Psuedo Ionone |
| 50 | 1-phenylethanone | Acetophenone |
| 51 | 2-butan-2-ylcyclohexan-1-one | Freskomenthe |
| 52 | Ethanone, 1-(3-methyl-2-benzofuranyl)- | nerolione |
| 53 | 4-(4-methoxyphenyl)butan-2-one | Anisyl Acetone |

The perfume raw material that formed the PRM fragment may be selected from the group consisting of the ketone-containing PRMs of Table C, above. The PRM that formed the PRM fragment may comprise a ketone moiety and may preferably be selected from the group consisting of: nerolione; 4-(4-methoxyphenyl)butan-2-one; 1-naphthalen-2-ylethanone; nectaryl; trimofix O; fleuramone; delta-damascone; beta-damascone; alpha-damascone; methyl ionone; 2-hexylcyclopent-2-en-1-one; galbascone; and mixtures thereof.

The benefit agent fragment may be derived from a benefit agent that is a perfume raw material, preferably a perfume raw material selected from the group consisting of: methyl nonyl acetaldehyde: benzaldehyde; floralozone; isocyclocitral; triplal (ligustral); precylcemone B; lilial; decyl aldehyde; undecylenic aldehyde; cyclamen homoaldehyde; cyclamen aldehyde; dupical; oncidal; adoxal; melonal; calypsone; anisic aldehyde; heliotropin; cuminic aldehyde; scentenal; 3,6-dimethylcyclohex-3-ene-1-carbaldehyde; satinaldehyde; canthoxal; vanillin; ethyl vanillin; cinnamic aldehyde; cis-4-decenal; trans-4-decenal; cis-7-decenal; undecylenic aldehyde; trans-2-hexenal; trans-2-octenal; 2-undecenal; 2,4-dodecadeienal; cis-4-heptenal; Florydral; cymal; butyl cinnamaldehyde; limonelal; amyl cinnamaldehyde; hexyl cinnamaldehyde; citronellal; citral; cis-3-hexen-1-al; nerolione; 4-(4-methoxyphenyl)butan-2-one; 1-naphthalen-2-ylethanone; nectaryl; trimofix O; fleuramone; delta-damascone; beta-damascone; alpha-damascone; methyl ionone; 2-hexylcyclopent-2-en-1-one; galbascone; and mixtures thereof.

When the benefit agent fragment is derived from a perfume raw material, preferably a PRM as listed in the previous paragraph, it may be preferred that the first monovalent moiety and/or the second monovalent moiety is an organic group comprising from about 8 to about 18 chain atoms, more preferably from about 10 to about 18 chain atoms, preferably wherein the chain atoms are carbon atoms. It is believed that such chain lengths provide a suitable degree of hydrophobicity to facilitate deposition benefits, particularly in laundry applications where the pro-benefit-agent compounds are used in aqueous liquors.

The perfumes raw materials in this specification, including the perfume raw materials listed above, can be obtained from various suppliers including: International Flavors and Fragrances of New York, NY USA; Givaudan of Vernier Switzerland; Firmenich of Geneva, Switzerland; Symrise of Holzminden, Germany; Kao of Tokyo, Japan; Takasago of Tokyo, Japan; and Florasynth of Tel-Aviv, Israel.

B. Anti-Microbial Agents

The benefit agent may be an anti-microbial agent that comprises an aldehyde moiety, a ketone moiety, or a mixture thereof.

Suitable anti-microbial agents for use in the present pro-benefit-agent compounds may include acetylacetone enolate, gossypol, nootkatone, or mixtures thereof.

When the benefit agent fragment is derived from an anti-microbial agent, preferably an anti-microbial agent as listed in the previous paragraph, it may be preferred that the hydrophobic moiety is an organic group comprising from about 6 to about 12 chain atoms, preferably wherein the chain atoms are carbon atoms. It is believed that such chain lengths provide a suitable degree of hydrophobicity to facilitate anti-microbial benefits and is believed to facilitate desired interactions between the anti-microbial agent and the target microbes.

Pro-Benefit-Agent Precursor Compounds

The present disclosure relates to pro-benefit-agent precursor compounds that are useful in making the pro-benefit-agent compounds described herein.

The pro-benefit-agent precursor compound (or simply "precursor compound" as used herein) may comprise a carbon-containing core, the carbon-containing core comprising a carbon backbone, one or more side groups, a nitrogen atom, and a carbonyl group, wherein the carbonyl group is part of a carbonyl-containing moiety that is selected from an ester moiety, an amide moiety, or a thioester moiety, wherein the carbonyl-containing moiety comprises a first heteroatom joined to the carbon of the carbonyl group, wherein the first heteroatom is selected from oxygen, nitrogen, or sulfur, wherein the carbonyl-containing moiety further comprises a first monovalent moiety joined to the first heteroatom, wherein the first monovalent moiety is an organic group comprising from 1 to 34 chain atoms; the nitrogen atom is preferably an amine group that comprises a substitution, where the substitution comprises a second heteroatom, the second heteroatom being selected from oxygen, nitrogen, or sulfur. The substitution on the amine group may further comprise a second monovalent moiety, as described above.

In effect, the precursor compound may be the pro-benefit-agent compound prior to its reaction with the (first) benefit agent. The cores, side groups, carbonyl-containing moieties, first monovalent moieties, and second monovalent moieties are preferably as previously described.

The pro-benefit-agent precursor compound may be characterized by a structure according to Formula VI:

$$HG'\text{-}(J)_{d'}\text{-}A\text{-}Q \qquad \text{Formula VI,}$$

where a J group is attached to the nitrogen atom of the A group, and A, J, index d, G', and Q are as substantially described above.

The precursor compound may be characterized by a structure according to Formula VII:

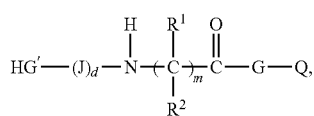

Formula VII wherein the groups and indices are as defined above.

The precursor compounds may be made by making modifications to a suitable parent core compound, such as a parent amino acid. For example, the carboxyl group of an amino acid with a compound according to the following formula H-G-Q, for example through an esterification, an amidation, or a thioesterification reaction. Suitable H-G-Q feedstocks may preferably be alcohols, fatty alcohols, and/or diols. The resulting compound may further be modified to make a heteroatom-containing substitution at the amine group. For example, the amine group may be reacted with an oxirane, resulting in an alkanolamine group. The alkanolamine group may then react with a suitable benefit agent to form a heterocyclic moiety.

Exemplary precursor compounds and methods of making such compounds are provided in the Synthetic Examples section below.

Methods of Making a Pro-Benefit-Agent Compound

The present disclosure also relates to methods of making a pro-benefit-agent compound. Such methods include the step of reacting a pro-benefit-agent precursor compound with a suitable benefit agent. Such precursor compounds and benefit agents are described above. Such reactions may occur in a premix composition, in a treatment composition, or even on a surface or an article, such as a fabric or a garment.

Exemplary methods of making such compounds are provided in the Synthetic Examples section below.

Premix Compositions

The present disclosure further relates to certain premix compositions and methods of making such compositions. Premixes can be conveniently prepared ahead of product formulation, and even prepared at one manufacturing site and shipped to another for product formulation.

The premix compositions may comprise a pro-benefit-agent precursor compound, where the precursor compound is as described above, and a benefit agent, where the benefit agent is as described above. The preferences expressed above for the pro-benefit-agent compound, its components, and/or its precursors apply equally here.

For example, the premix composition may comprise: a pro-benefit-agent precursor compound, wherein the precursor compound is characterized by a structure according to Formula VII:

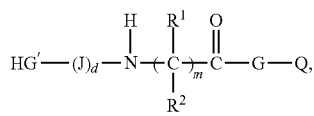

Formula VII wherein the groups and indices are as defined above; and a benefit agent, the benefit agent comprising an aldehyde moiety, a ketone moiety, or combinations thereof.

For loading efficiency reasons, it is preferred to reasonably match the molar amount of the benefit agent, preferably a first benefit agent, with the molar amount of the carrier molecules as described above (here, the pro-benefit-agent precursor compound). For example, the premix composition may comprise the pro-benefit-agent precursor compound and the benefit agent in a molar ratio of from about 3:1 to about 1:3, preferably from about 2:1 to about 1:2, preferably from about 1.5:1 to about 1:1.5, more preferably from about 1.2:1 to about 1:1.2, even more preferably from about 1:1.

Even more specifically, for loading efficiency reasons, it is preferred to reasonably match the molar amount of the benefit agent with the molar equivalent of the reacting functional groups (e.g., preferably amine groups) of the carrier molecules as described above (here, the pro-benefit-agent precursor compound). For example, the premix composition may comprise the reacting functional groups (e.g., preferably amine groups) of the pro-benefit-agent precursor compound and benefit agent in a molar ratio of from about 3:1 to about 1:3, preferably from about 2:1 to about 1:2, preferably from about 1.5:1 to about 1:1.5, more preferably from about 1.2:1 to about 1:1.2, even more preferably from about 1:1.

When the pro-benefit-agent precursor compound comprises multiple attachment points, or multiple functional groups capable of forming such attachment points, for the benefit agent and optionally a second benefit agent, the premix composition may include such functional groups of the pro-benefit-agent precursor compound and the benefit agent (plus optionally a second benefit agent that is also capable of attaching to the precursor compound) present in a molar ratio of from about 3:1 to about 1:3, preferably from about 2:1 to about 1:2, preferably from about 1.5:1 to about 1:1.5, more preferably from about 1.2:1 to about 1:1.2, even more preferably from about 1:1. Such ratios may be useful to maximize the loading and/or delivery efficiency.

The premix composition may be in the form of a neat fluid, and little to no water may be present. In such cases, it may be desirable to include a water scavenger such as magnesium sulfate in the premix, and/or to physically remove water, such as via a molecular sieve or in vacuo. The premix composition may comprise less than about 10%, preferably less than 5%, more preferably less than 1%, even more preferably less than 0.1% water, by weight of the premix composition. Low-water premix compositions may be particularly preferred when they are intended to be formulated into low-water product compositions, such as solids like pastilles, or compact formulations like unit dose compositions that are encapsulated in water-soluble films. When the premix is a low-water premix, the premix may comprise from about 1% to about 100%, preferably from about 5% to about 100%, more preferably from about 20% to about 100%, by weight of the premix composition, of the pro-benefit-agent compound. When the premix is a low water premix, the premix may comprise from about 0.01% to about 80%, preferably from about 0.01% to about 20%, by weight of the premix composition, of the pro-benefit agent precursor compound. When the premix is a low-water premix, the premix may comprise from about 0.01% to about 80%, preferably from about 0.01% to about 20%, by weight of the premix composition, of the benefit agent.

The premix composition may comprise water. The premix composition may be in the form of an emulsion, preferably an oil-in-water emulsion. When the premix is in the form of an emulsion and comprises water, water may be present at a level of from about 50% to about 95%, preferably from about 60% to about 90%, by weight of the premix composition. When the premix comprises water, the pro-benefit-agent precursor compound may be added at a level of from about 0.01% to about 7.5%, by weight of the premix composition. When the premix comprises water, the benefit agent may be added at a level of from about 0.01% to about 7.5%, by weight of the premix composition.

In the premix composition, the precursor compound and the benefit agent may react to form a pro-benefit-agent compound, as described above. The precursor compound, the benefit agent, and the pro-benefit-agent compound may all be present in an equilibrium. Because the formation of a pro-benefit-agent compound according to the present disclosure typically produces water through a condensation process to form a heterocyle, the equilibrium may be tilted towards the reactant side (e.g., precursor compound and benefit agent) of the reaction when the premix comprises water. Vice versa, relatively more of the pro-benefit-agent compound may be present when the premix is substantially free of intentionally added water, although it is recognized that water forms as a result of the condensation reaction.

The sum of the weight percents of the pro-benefit-agent precursor, the benefit agent, and the pro-benefit-agent compound, if present, may be from about 10% to about 100%, preferably from about 25% to about 100%, more preferably from about 50% to about 100%, even more preferably from about 75% to about 100%, by weight of the premix composition.

The premix composition, or a portion thereof, may be obtained by combining from about 1 part to about 99 parts, preferably from about 5 to about 80 parts, by weight of the pro-benefit-agent precursor compound with about 1 part to about 99 parts, preferably from about 5 to about 80 parts, by weight of the benefit agent, wherein the resulting mixture is understood to comprise a total of 100 parts by weight.

The premix composition may include multiple precursors, multiple benefit agent, and/or multiple pro-benefit-agent compounds. The premix composition may further comprise additional agents that do not react to form pro-benefit-agent compounds according to the present disclosure. For example, the premix compositions may comprise additional PRMs, surfactants, solvents, or other processing or stability aids.

The premix composition may comprise a surfactant, preferably a nonionic surfactant. Surfactants may help with stability of the premix compositions, and/or with the emulsification process.

The present disclosure also relates to methods of making such premix compositions. The method may include the steps of combining a pro-benefit-agent precursor as described herein (e.g., according to Formulas IV or V above) with a benefit agent as described herein, wherein the benefit agent comprises an aldehyde moiety, a ketone moiety, or a combination thereof. The materials may combined in the proportions provided above. The method may include removing or otherwise binding free water, which may help to drive the reaction in the premix towards the product (e.g., the pro-benefit-agent compound). When the premix composition comprises water, the precursor compound and the water may preferably be combined before the benefit agent is added. Alternatively, the benefit agent and the water may be combined before the benefit agent is added.

Treatment Composition

The present composition relates to treatment compositions that include an adjunct ingredient and a pro-benefit-agent compound, as described above.

The treatment compositions may be consumer product compositions. The consumer products compositions of the present disclosure may be useful in baby care, beauty care, fabric care, home care, family care, feminine care, and/or health care applications. The treatment compositions may be useful for treating a surface, such as fabric, hair, or skin. The consumer product compositions may be intended to be used or consumed in the form in which it is sold. The consumer product compositions may be not intended for subsequent commercial manufacture or modification.

The treatment composition may be a household care composition. The treatment composition may be a fabric care composition, a hard surface cleaner composition, a dish care composition, a hair care composition (such as shampoo or conditioner), a body cleansing composition, or a mixture thereof.

The treatment composition may be a fabric care composition, such as a laundry detergent composition (including a heavy-duty liquid washing detergent or a unit dose article), a fabric conditioning composition (including a liquid fabric softening and/or enhancing composition), a laundry additive, a fabric pre-treat composition (including a spray, a pourable liquid, or a spray), a fabric refresher composition (including a spray), or a mixture thereof.

The treatment composition may be a beauty care composition, such as a hair treatment product (including shampoo and/or conditioner), a skin care product (including a cream, lotion, or other topically applied product for consumer use), a shave care product (including a shaving lotion, foam, or pre- or post-shave treatment), personal cleansing product (including a liquid body wash, a liquid hand soap, and/or a bar soap), a deodorant and/or antiperspirant, or mixtures thereof.

The treatment composition may be a home care composition, such as an air care, car care, dishwashing, hard surface cleaning and/or treatment, and other cleaning for consumer or institutional use.

The treatment composition may be in the form of a liquid composition, a granular composition, a hydrocolloid, a single-compartment pouch, a multi-compartment pouch, a dissolvable sheet, a pastille or bead, a fibrous article, a tablet, a stick, a bar, a flake, a foam/mousse, a non-woven sheet, or a mixture thereof.

The treatment composition may be in the form of a liquid. The liquid composition may include from about 30%, or from about 40%, or from about 50%, to about 99%, or to about 95%, or to about 90%, or to about 75%, or to about 70%, or to about 60%, by weight of the composition, of water. The liquid composition may be a liquid laundry detergent, a liquid fabric conditioner, a liquid dish detergent, a hair shampoo, a hair conditioner, or a mixture thereof.

The treatment composition may be in the form of a solid. The solid composition may be a powdered or granular composition. Such compositions may be agglomerated or spray-dried. Such composition may include a plurality of granules or particles, at least some of which include comprise different compositions. The composition may be a powdered or granular cleaning composition, which may include a bleaching agent. The composition may be in the form of a bead or pastille, which may be pastilled from a liquid melt. The composition may be an extruded product.

The treatment composition may be in a particulate form, such as a plurality of particulates. Individual particulates may have a mass from about 1 mg to about 1 g. The emulsion may be dispersed in a water-soluble carrier. The water-soluble carrier may be selected from the group consisting of polyethylene glycol, sodium acetate, sodium bicarbonate, sodium chloride, sodium silicate, polypropylene glycol polyoxoalkylene, polyethylene glycol fatty acid ester, polyethylene glycol ether, sodium sulfate, starch, and mixtures thereof. The water-soluble carrier may be a water-soluble polymer. The treatment composition, when in particulate form, may comprise from about 25 wt % to about 99.99 wt % of the water-soluble carrier, and from about 0.001 wt % to about 50 wt % by weight the pro-benefit-agent compound. The particulate form may be in the form of a bead or pastille.

The treatment composition may be in the form of a unitized dose article, such as a tablet, a pouch, a sheet, or a fibrous article. Such pouches typically include a water-soluble film, such as a polyvinyl alcohol water-soluble film, that at least partially encapsulates a composition. Suitable films are available from MonoSol, LLC (Indiana, USA). The composition can be encapsulated in a single or multi-compartment pouch. A multi-compartment pouch may have at least two, at least three, or at least four compartments. A multi-compartmented pouch may include compartments that are side-by-side and/or superposed. The composition contained in the pouch or compartments thereof may be liquid, solid (such as powders), or combinations thereof. Pouched compositions may have relatively low amounts of water, for example less than about 20%, or less than about 15%, or less than about 12%, or less than about 10%, or less than about 8%, by weight of the detergent composition, of water.

The treatment composition may be in the form of a spray and may be dispensed, for example, from a bottle via a trigger sprayer and/or an aerosol container with a valve.

The treatment composition may have a viscosity of from 1 to 1500 centipoises (1-1500 mPa*s), from 100 to 1000 centipoises (100-1000 mPa*s), or from 200 to 500 centipoises (200-500 mPa*s) at 20 s$^{-1}$ and 21° C.

The treatment composition may comprise from about 0.001% to about 30%, preferably from about 0.001% to about 20%, more preferably from about 0.001% to about 15%, 0.001% to about 10%, preferably from about 0.01% to about 5%, by weight of the treatment composition, of the pro-benefit-agent compound.

The treatment composition may comprise the pro-benefit-agent compound in an amount sufficient to deliver from about 0.01% to about 10%, preferably from about 0.1% to about 5%, by weight of the treatment composition, of the benefit agent that is to be released by the pro-benefit-agent compound.

Adjunct Ingredient

The treatment compositions of the present disclosure, which may be consumer products, may comprise an adjunct material. The adjunct material may provide a benefit in the intended end-use of a composition, or it may be a processing and/or stability aid.

Suitable adjunct materials may include: surfactants, conditioning actives, deposition aids, rheology modifiers or structurants, antioxidants, bleach systems, stabilizers, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, silicones, hueing agents, aesthetic dyes, neat perfume, perfume delivery systems, structure elasticizing agents, carriers, hydrotropes, processing aids, anti-agglomeration agents, coatings, formaldehyde scavengers, and/or pigments.

Depending on the intended form, formulation, and/or end-use, compositions of the present disclosure or may not may not contain one or more of the following adjunct materials: surfactants, conditioning actives, deposition aids, rheology modifiers or structurants, antioxidants, bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes, perfume delivery systems, structure elasticizing agents, fabric softeners, carriers, hydrotropes, processing aids, structurants, anti-agglomeration agents, coatings, formaldehyde scavengers and/or pigments.

The precise nature of these additional components, and levels of incorporation thereof, will depend on the physical form of the composition and the nature of the operation for which it is to be used. However, when one or more adjuncts are present, such one or more adjuncts may be present as detailed below. The following is a non-limiting list of suitable additional adjuncts.

A. Surfactants

The treatment compositions of the present disclosure may comprise surfactant. Surfactants may be useful for providing, for example, cleaning benefits. The compositions may comprise a surfactant system, which may contain one or more surfactants.

The treatment compositions of the present disclosure may include from about 0.1% to about 70%, or from about 2% to about 60%, or from about 5% to about 50%, by weight of the composition, of a surfactant system. Liquid compositions may include from about 5% to about 40%, by weight of the composition, of a surfactant system. Compact formulations, including compact liquids, gels, and/or compositions suitable for a unit dose form, may include from about 25% to about 70%, or from about 30% to about 50%, by weight of the composition, of a surfactant system.

The surfactant system may include anionic surfactant, nonionic surfactant, zwitterionic surfactant, cationic surfactant, amphoteric surfactant, or combinations thereof. The surfactant system may include linear alkyl benzene sulfonate, alkyl ethoxylated sulfate, alkyl sulfate, nonionic surfactant such as ethoxylated alcohol, amine oxide, or mixtures thereof. The surfactants may be, at least in part, derived from natural sources, such as natural feedstock alcohols.

Suitable anionic surfactants may include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The anionic surfactants may be linear, branched, or combinations thereof. Preferred surfactants include linear alkyl benzene sulfonate (LAS), alkyl ethoxylated sulfate (AES), alkyl sulfates (AS), or mixtures thereof. Other suitable anionic surfactants include branched modified alkyl benzene sulfonates (MLAS), methyl ester sulfonates (MES), sodium lauryl sulfate (SLS), sodium lauryl ether sulfate (SLES), and/or alkyl ethoxylated carboxylates (AEC). The anionic surfactants may be present in acid form, salt form, or mixtures thereof. The anionic surfactants may be neutralized, in part or in whole, for example, by an alkali metal (e.g., sodium) or an amine (e.g., monoethanolamine).

The surfactant system may include nonionic surfactant. Suitable nonionic surfactants include alkoxylated fatty alcohols, such as ethoxylated fatty alcohols. Other suitable nonionic surfactants include alkoxylated alkyl phenols, alkyl phenol condensates, mid-chain branched alcohols, mid-chain branhed alkyl alkoxylates, alkylpolysaccharides (e.g., alkylpolyglycosides), polyhydroxy fatty acid amides, ether capped poly(oxyalkylated) alcohol surfactants, and mixtures thereof. The alkoxylate units may be ethyleneoxy units, propyleneoxy units, or mixtures thereof. The nonionic surfactants may be linear, branched (e.g., mid-chain branched), or a combination thereof. Specific nonionic surfactants may include alcohols having an average of from about 12 to about 16 carbons, and an average of from about 3 to about 9 ethoxy groups, such as C12-C14 EO7 nonionic surfactant.

Suitable zwitterionic surfactants may include any conventional zwitterionic surfactant, such as betaines, including alkyl dimethyl betaine and cocodimethyl amidopropyl betaine, $C_8$ to $C_{18}$ (for example from $C_{12}$ to $C_{18}$) amine oxides (e.g., $C_{12-14}$ dimethyl amine oxide), and/or sulfo and hydroxy betaines, such as N-alkyl-N,N-dimethylamino-1-propane sulfonate where the alkyl group can be $C_8$ to $C_{18}$, or from $C_{10}$ to $C_{14}$. The zwitterionic surfactant may include amine oxide.

Depending on the formulation and/or the intended end-use, the composition may be substantially free of certain surfactants. For example, liquid fabric enhancer compositions, such as fabric softeners, may be substantially free of anionic surfactant, as such surfactants may negatively interact with cationic ingredients.

B. Conditioning Active

The treatment compositions of the present disclosure may include a conditioning active. Compositions that contain conditioning actives may provide softness, anti-wrinkle, anti-static, conditioning, anti-stretch, color, and/or appearance benefits.

Conditioning actives may be present at a level of from about 1% to about 99%, by weight of the composition. The composition may include from about 1%, or from about 2%, or from about 3%, to about 99%, or to about 75%, or to about 50%, or to about 40%, or to about 35%, or to about 30%, or to about 25%, or to about 20%, or to about 15%, or to about 10%, by weight of the composition, of conditioning active. The composition may include from about 5% to about 30%, by weight of the composition, of conditioning active.

Conditioning actives suitable for compositions of the present disclosure may include quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, polyhydroxystearic acid and/or derivatives thereof, glyceride copolymers, or combinations thereof. Preferably, the conditioning active is a cationic conditioning active, which may improve the delivery/deposition of the pro-benefit-agent compound.

The treatment composition may comprise a conditioning active, where the conditioning active comprises quaternary ammonium ester compounds. Preferably, the quaternary ammonium ester compounds are present at a level of from about 2 wt % to about 35 wt %, preferably from about 4 wt % to about 25 wt %, more 5 wt % to about 20 wt %, even more preferably from about 6 wt % to about 15 wt %, even more preferably from about 7 wt % to about 12 wt %, by weight of the treatment composition. The quaternary ammonium ester compounds (also known as "ester quats") may be monoester quats, diester quats, triester quats, or a combination thereof; preferably, diester quat material forms the major portion (whether a majority or a plurality) of the ester quat compounds. It is believed that in addition to providing conditioning benefits, selecting the proper type and/or level of conditioning active (namely, a quaternary ammonium ester compound) can improve the deposition and/or performance of the pro-benefit-agent compounds described in the present disclosure.

The quaternary ammonium ester compound may comprise compounds according to the following formula:

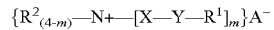

wherein:
  m is 1, 2 or 3, with provisos that, in a given molecule, the value of each m is identical;
  each $R^1$, which may comprise from 13 to 22 carbon atoms, is independently a linear hydrocarbyl or branched hydrocarbyl group, preferably $R^1$ is linear, more preferably $R^1$ is partially unsaturated linear alkyl chain;
  each $R_2$ is independently a $C_1$-$C_3$ alkyl or hydroxyalkyl group and/or each $R_2$ is selected from methyl, ethyl, propyl, hydroxyethyl, 2-hydroxypropyl, 1-methyl-2-hydroxyethyl, poly($C_2$-$C_3$ alkoxy), polyethoxy, benzyl, more preferably methyl or hydroxyethyl;
  each X is independently —($CH_2$)n-, —$CH_2$—CH($CH_3$)— or —CH($CH_3$)—$CH_2$—, where each n is independently 1, 2, 3 or 4, preferably each n is 2;
  each Y is independently —O—(O)C— or —C(O)—O—; and
  A– is independently selected from the group consisting of chloride, bromide, methyl sulfate, ethyl sulfate, sulfate, and nitrate, preferably A– is selected from the group consisting of chloride and methyl sulfate, more preferably A– is methyl sulfate.

For monoester quats, m is 1. For diester quats, m is 2. For triester quats, m is 3. The conditioning active may comprise a mixture of monoester quats and diester quats, or even a mixture of monoester quats, diester quats, and triester quats. As will be appreciated by one of ordinary skill, the mixture may depend, in part, on the starting/feedstock materials, such dialkanolamines or trialkanolamines.

The quaternary ammonium ester compound may be derived from fatty acids characterized by an Iodine Value of from 0 to 140, or from 0 to about 90, or from about 10 to about 70, or from about 15 to about 50, or from about 18 to about 30. Iodine Values may be determined according to the method provided in US2020/0407665 (equivalent to WO2020/264566).

The composition may include a quaternary ammonium ester compound, a silicone, or combinations thereof, preferably a combination. The combined total amount of quaternary ammonium ester compound and silicone may be from about 5% to about 70%, or from about 6% to about 50%, or from about 7% to about 40%, or from about 10% to about 30%, or from about 15% to about 25%, by weight of the composition. The composition may include a quaternary ammonium ester compound and silicone in a weight ratio of from about 1:10 to about 10:1, or from about 1:5 to about 5:1, or from about 1:3 to about 1:3, or from about 1:2 to about 2:1, or about 1:1.5 to about 1.5:1, or about 1:1.

The composition may contain mixtures of different types of conditioning actives. The compositions of the present disclosure may contain a certain conditioning active but be substantially free of others. For example, the composition may be free of quaternary ammonium ester compounds, silicones, or both. The composition may comprise quaternary ammonium ester compounds but be substantially free of silicone. The composition may comprise silicone but be substantially free of quaternary ammonium ester compounds.

The conditioning active may comprise glyceride copolymers. The glyceride copolymers may be derived from natural oils. Examples of natural oils include, but are not limited to, vegetable oils, algae oils, fish oils, animal fats, tall oils, derivatives of these oils, combinations of any of these oils, and the like. Representative non-limiting examples of vegetable oils include low erucic acid rapeseed oil (canola oil), high erucic acid rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil, preferably canola oil. Representative non-limiting examples of animal fats include lard, tallow, poultry fat, yellow grease, and fish oil. Tall oils are by-products of wood pulp manufacture. The glyceride copolymers may be metathesized unsaturated polyol esters.

C. Deposition Aid

The treatment compositions of the present disclosure may comprise a deposition aid.

Deposition aids can facilitate deposition of the various benefit agents, including the pro-benefit-agent compounds of the present disclosure, conditioning actives, perfumes or perfume delivery systems (such as encapsulated perfumes), or combinations thereof, improving the performance benefits of the compositions and/or allowing for more efficient formulation of such benefit agents. The composition may comprise, by weight of the composition, from 0.0001% to 3%, preferably from 0.0005% to 2%, more preferably from 0.001% to 1%, or from about 0.01% to about 0.5%, or from about 0.05% to about 0.3%, of a deposition aid. The deposition aid may be a cationic or amphoteric polymer, preferably a cationic polymer.

Cationic polymers in general and their methods of manufacture are known in the literature. Suitable cationic polymers may include quaternary ammonium polymers known the "Polyquaternium" polymers, as designated by the International Nomenclature for Cosmetic Ingredients, such as Polyquaternium-6 (poly(diallyldimethylammonium chloride), Polyquaternium-7 (copolymer of acrylamide and diallyldimethylammonium chloride), Polyquaternium-10 (quaternized hydroxyethyl cellulose), Polyquaternium-22 (copolymer of acrylic acid and diallyldimethylammonium chloride), and the like.

The deposition aid may be selected from the group consisting of polyvinylformamide, partially hydroxylated polyvinylformamide, polyvinylamine, polyethylene imine, ethoxylated polyethylene imine, polyvinylalcohol, polyacrylates, and combinations thereof.

The cationic polymer may comprise a cationic acrylate and/or cationic methacrylate. Such polymers may be copolymers, for example further comprising a nonionic monomer, such as acrylamide. The cationic polymer may be linear or crosslinked. The deposition aid may comprise a combination of linear cationic polymers and crosslinked cationic polymers.

Deposition aids can be added concomitantly with delivery particles (at the same time with, e.g., encapsulated benefit agents, such as the encapsulated perfume) or directly/independently in the consumer product composition. The weight-average molecular weight of the polymer may be from 500 to 5000000 or from 1000 to 2000000 or from 2500 to 1500000 Dalton, as determined by size exclusion chromatography relative to polyethyleneoxide standards using Refractive Index (RI) detection. The weight-average molecular weight of the cationic polymer may be from 5000 to 37500 Dalton.

D. Perfume and/or Perfume Delivery Systems

The treatment compositions of the present disclosure may comprise perfume and/or perfume delivery systems. This may be the case even when the benefit agent fragment of the pro-benefit-agent compound is derived from a perfume raw material.

The treatment compositions of the present disclosure may comprise other perfume raw materials, for example in neat or free form, including PRMs that do not contain an aldehyde or ketone moiety. For example, other PRMs may be provided as neat or free oils to the premix composition and/or the treatment compositions according to the present disclosure, even if they will not react with the pro-benefit-agent precursor compound. Such mixtures may be desirable, for example, to provide a more well-rounded olfactory experience.

The treatment compositions of the present disclosure may further comprise neat perfume, preferably neat perfume raw materials that does not comprise an aldehyde or ketone moiety. Preferably, the neat perfume comprises an alcohol-containing perfume raw material. Suitable alcohol-containing perfume raw materials are known to one of ordinary skill in the art, and may include geraniol, citronellol, cinnamic alcohol, eugenol, and the like. That being said, the neat perfume may further comprise free perfume raw materials that do comprise aldehyde and/or ketone moieties.

The treatment compositions of the present disclosure may, additionally or alternatively, comprise a perfume delivery system. Such perfume delivery systems may take the form of a polymer-assisted delivery system. Such perfume delivery systems may take the form of an encapsulate, for example a core-shell encapsulate, where the core comprises perfume raw materials and is surrounded by a polymeric shell. The polymeric shell may comprise polymeric material derived from polyacrylates, polyurea, polyurethanes, polysaccharides, polyvinyl alcohol, melamine, derivatives thereof, or combinations thereof. Additionally or alternatively, suitable perfume delivery systems may include known pro-perfume/pro-fragrance materials.

Other Materials

The treatment compositions, and/or even the premix compositions, of the present disclosure may comprise unreacted reactants and/or degradation products of the pro-benefit-agent compounds described herein. For example, the treatment compositions and/or premix compositions of the present disclosure may comprise: precursors or derivatives of the carbon-containing core alone, such as parent amino acids (e.g., $H_2$-A-H, where A is substantially as defined above according to Formula III, where G=oxygen); modified amino acids having a first monovalent moiety (e.g., $H_2$-A-Q, where A is substantially as defined above according to Formula III); free forms of the first monovalent moiety (e.g., H-G-Q, such as fatty alcohols like Dodecanol); forms of the pro-benefit-agent compounds that are free of the first monovalent moiety (e.g, including the heterocylic moiety but not the first monovalent moiety); free benefit agents, such as aldehyde- or ketone-containing PRMs; or combinations thereof. Other materials that may be present can include solvents or diluents, free oxirane precursors, residual catalytic salts, or combinations thereof.

Method of Making a Treatment Composition

The present disclosure relates to processes for making any of the compositions described herein. The process of making a treatment composition, which may be a consumer product, may comprise the step of combining a pro-benefit-agent compound as described herein with an adjunct material as described herein.

The pro-benefit-agent compound may be combined with such adjunct materials by methods that include mixing and/or spraying.

The compositions of the present disclosure can be formulated into any suitable form and prepared by any process chosen by the formulator. The pro-benefit-agent compounds and adjunct materials may be combined in a batch process, in a circulation loop process, and/or by an in-line mixing process. Suitable equipment for use in the processes disclosed herein may include continuous stirred tank reactors, homogenizers, turbine agitators, recirculating pumps, paddle mixers, high shear mixers, static mixers, plough shear mixers, ribbon blenders, vertical axis granulators and drum mixers, both in batch and, where available, in continuous process configurations, spray dryers, and extruders.

For example, the method of making a treatment composition may include the step of combining a pro-benefit-agent compound according to the present disclosure with a base composition, preferably a liquid base composition, where the base composition comprises an adjunct ingredient. This process may occur, for example, in a batch process or in an in-line mixing process, preferably an in-line mixing process.

The method of making a treatment composition may include the step of combining a pro-benefit-agent precursor compound, a benefit agent, and an adjunct ingredient, as described herein. Preferably, the adjunct ingredient is part of a base composition, and the pro-benefit-agent precursor compound and the benefit agent are each added to the base composition as separate inputs. The separate inputs may be added sequentially (e.g. in series), or substantially simultaneously. Preferably, the base composition is a liquid. This process may occur, for example, in a batch process or in an in-line mixing process, preferably an in-line mixing process.

The method of making a treatment composition may include the step of adding a premix to a base composition. The premix composition may comprise a pro-benefit-agent precursor compound and a benefit agent, as described herein. The premix composition may be obtainable by combining a pro-benefit-agent precursor compound and a benefit agent, as described herein. The premix composition may include a pro-benefit-agent compound according to the present disclosure, for example due to the reaction of the precursor compound and the benefit agent. The premix composition may include a mixture of a pro-benefit agent precursor compound, a benefit agent, and a pro-benefit-agent compound. The premix may optionally contain water. This process may occur, for example, in a batch process or in an in-line mixing process, preferably an in-line mixing process. A premix may be particularly preferred when making a treatment composition that is in, or will be in solid form, such as a PEG-based pastille. In such cases, removal or reduction of water from the premix may be useful, for example via a water scavenger such as magnesium sulfate, or via the use of a molecular sieve or distilled off in vacuo.

Method of Treating a Surface

The present disclosure further relates to methods of treating a surface (for example, a surface of an article) with a treatment composition according to the present disclosure. Such methods may provide cleaning, conditioning, hygiene, and/or freshening benefits.

Suitable surfaces may include fabrics (including clothing, towels, or linens), hard surfaces (such as tile, porcelain, linoleum or wood floors), dishware, hair, skin, or mixtures thereof.

The method may include a step of contacting an article or surface with a treatment composition of the present disclosure, optionally in the presence of water, optionally further including the step of rinsing and/or drying the article or surface The treatment composition may be in neat form or diluted in a liquor, for example, a wash or rinse liquor. The treatment composition may be diluted in water prior, during, or after contacting the surface or article. The surface, or an article comprising such a surface, may be optionally washed and/or rinsed before and/or after the contacting step.

The method of treating and/or cleaning a surface may include the steps of:
a) optionally washing, rinsing and/or drying the surface;
b) contacting the surface with a treatment composition as described herein, optionally in the presence of water;
c) optionally washing and/or rinsing the surface; and
d) optionally drying the surface by drying passively and/or via an active method such as a laundry dryer.

For purposes of the present invention, washing includes but is not limited to, scrubbing, and mechanical agitation. The fabric may comprise most any fabric capable of being laundered or treated in normal consumer or industrial use conditions.

Liquors that may comprise the disclosed compositions may have a pH of from about 3 to about 11.5. When diluted, such compositions are typically employed at concentrations of from about 500 ppm to about 15,000 ppm in solution. When the wash solvent is water, the water temperature typically ranges from about 5° C. to about 90° C. and, when the surface is part of a fabric, the water to fabric weight ratio is typically from about 1:1 to about 30:1.

The present disclosure further discloses a process of treating a surface or article, preferably a fabric, with an aqueous treatment liquor that comprises a pro-benefit-agent compound according to the present disclosure, preferably where the benefit agent fragment is a fragment of a perfume raw material or an antimicrobial agent, preferably a fragment of a perfume raw material. The process may include the step of contacting the surface or article, preferably a fabric, with the aqueous liquor. The pro-benefit-agent compound may be present in the aqueous liquor at a level of from about 0.001 ppm (e.g., 1 ppb) to about 1000 ppm by weight.

The present disclosure further discloses a process of treating a surface or article, preferably a fabric, with an aqueous treatment liquor that comprises the pro-benefit-agent precursor compound according to the present disclosure, and a benefit agent according to the present disclosure. The benefit agent may be a perfume raw material or an antimicrobial agent, preferably perfume raw material. The process may include the step of contacting the surface or article, preferably a fabric, with the aqueous liquor. The pro-benefit-agent precursor compound may be present in the aqueous liquor at a level of from about 0.001 ppm (e.g., 1 ppb) to about 1000 ppm by weight.

Use

The present disclosure relates to the use of the presently described pro-benefit-agent compounds for providing a freshness benefit when the pro-benefit-agent compound comprises a fragment of a perfume raw material, particularly when part of a treatment composition.

The present disclosure relates to the use of the presently described pro-benefit-agent compounds for providing an antimicrobial benefit when the pro-benefit-agent compound comprises a fragment of an antimicrobial agent, particularly when part of a treatment composition.

The present disclosure relates to the use of the presently described pro-benefit-agent compounds for providing an anti-malodor benefit, particularly when part of a treatment composition.

Combinations

Specifically contemplated combinations of the disclosure are herein described in the following lettered paragraphs. These combinations are intended to be illustrative in nature and are not intended to be limiting.

A. A pro-benefit-agent compound, where the compound comprises: a carbon-containing core, the carbon-containing core comprising a carbon backbone, one or more side groups, a nitrogen atom, and a carbonyl group, wherein the carbonyl group is part of a carbonyl-containing moiety that is selected from an ester moiety, an amide moiety, or a thioester moiety, wherein the carbonyl-containing moiety comprises a first heteroatom joined to the carbon of the carbonyl group, wherein the first heteroatom is selected from oxygen, nitrogen, or sulfur, wherein the carbonyl-containing moiety further comprises a first monovalent moiety joined to the first heteroatom, wherein the first monovalent moiety is an organic group comprising from 1 to 34 chain atoms; a benefit agent fragment, wherein a carbon atom of the benefit agent fragment, the nitrogen of the carbon-containing core, and a second heteroatom are part of a heterocyclic moiety, wherein the second heteroatom is selected from oxygen, nitrogen, or sulfur, wherein the second heteroatom is not part of a side group of the core, wherein the carbon atom of the benefit agent fragment is bonded to the nitrogen and the second heteroatom, and wherein the benefit agent fragment is derived from a benefit agent, the benefit agent comprising an aldehyde moiety, a ketone moiety, or combinations thereof, wherein the heterocyclic moiety optionally further comprises a second monovalent moiety that is an organic group comprising from 1 to 34 chain atoms, preferably carbon atoms; wherein at least one of the following is true: (a) at least one of the first monovalent moiety and the second monovalent moiety, if present, comprises at least five, preferably at least eight, chain atoms, preferably carbon atoms, and/or (b) the second monovalent moiety is present, and the sum of the number of chain atoms, preferably carbon chain atoms, in the first monovalent moiety and the second monovalent moiety is at least eight.

B. The pro-benefit-agent compound according to paragraph A, wherein the carbon backbone comprises from one to six carbon atoms, preferably from one to three carbon atoms, more preferably one carbon atom.

C. The pro-benefit-agent compound according to any of paragraphs A or B, wherein the carbon-containing core is derived from an amino acid, preferably a proteinogenic amino acid, more preferably a proteinogenic amino acid selected from the group consisting of alanine, glycine, valine, phenylalanine, leucine, isoleucine, or combinations thereof, even more preferably a proteinogenic amino acid selected from the group consisting of alanine, glycine, or combinations thereof.

D. The pro-benefit-agent compound according to any of paragraphs A-C, wherein at least one side group has the structure of a side group of a proteinogenic amino acid or a derivative thereof, preferably the side group of a proteinogenic amino acid selected from the group consisting of valine, phenylalanine, leucine, isoleucine, alanine, glycine, a derivative thereof, or combinations thereof, more preferably alanine, glycine, a derivative thereof, or combinations thereof.

E. The pro-benefit-agent compound according any of paragraphs A-D, wherein the carbonyl-containing moiety is an ester moiety.

F. The pro-benefit-agent compound according any of paragraphs A-E, wherein at least one of the first monovalent moiety and the second monovalent moiety is an organic group comprising from about 8 to about 18 chain atoms, preferably from about 8 to about 14 chain atoms, more preferably carbon chain atoms.

G. The pro-benefit-agent compound according to any of paragraphs A-F, wherein at least one of the first monovalent moiety and the second monovalent moiety is an unsubstituted organic group, an unbranched organic group, or a combination thereof, preferably a combination thereof.

H. The pro-benefit-agent compound according any of paragraphs A-G, wherein the benefit agent fragment is derived from a benefit agent that comprises an aldehyde moiety, preferably derived from a perfume raw material that comprises an aldehyde moiety.

I. The pro-benefit-agent compound according any of paragraphs A-H, wherein the benefit agent fragment is derived from a benefit agent that comprises a ketone moiety, preferably derived from a perfume raw material that comprises a ketone moiety.

J. The pro-benefit-agent compound according any of paragraphs A-I, wherein benefit agent fragment is derived from a benefit agent that is selected from a perfume raw material, an antimicrobial agent, a pesticide, an insect repellant, an anti-fungal agent, a herbicidal agent, hueing dyes, antioxidants, non-perfume organoleptics, or a combination thereof, preferably a perfume raw material, an antimicrobial, or combinations thereof.

K. The pro-benefit-agent compound according any of paragraphs A-J, wherein the benefit agent is a perfume raw material, preferably a perfume raw material selected from the group consisting of: methyl nonyl acetaldehyde: benzaldehyde; floralozone; isocyclocitral; triplal (ligustral); precylcemone B; lilial; decyl aldehyde; undecylenic aldehyde; cyclamen homoaldehyde; cyclamen aldehyde; dupical; oncidal; adoxal; melonal; calypsone; anisic aldehyde; heliotropin; cuminic aldehyde; scentenal; 3,6-dimethylcyclohex-3-ene-1-carbaldehyde; satinaldehyde; canthoxal; vanillin; ethyl vanillin; cinnamic aldehyde; cis-4-decenal; trans-4-decenal; cis-7-decenal; undecylenic aldehyde; trans-2-hexenal; trans-2-octenal; 2-undecenal; 2,4-dodecadeienal; cis-4-heptenal; Florydral; butyl cinnamaldehyde; limonelal; amyl cinnamaldehyde; hexyl cinnamaldehyde; citronellal; citral; cis-3-hexen-1-al; nerolione; 4-(4-methoxyphenyl)butan-2-one; 1-naphthalen-2-ylethanone; nectaryl; trimofix O; fleuramone; delta-damascone; beta-damascone; alpha-damascone; methyl ionone; 2-hexylcyclopent-2-en-1-one; galbascone; and mixtures thereof; more preferably an aldehyde-containing perfume raw material selected from the group consisting of: methyl nonyl acetaldehyde: benzaldehyde; floralozone; isocyclocitral; triplal (ligustral); precylcemone B; lilial; decyl aldehyde; undecylenic aldehyde; cyclamen homoaldehyde; cyclamen aldehyde; dupical; oncidal; adoxal; melonal; calypsone; anisic aldehyde; heliotropin; cuminic aldehyde; scentenal; 3,6-dimethylcyclohex-3-ene-1-carbaldehyde; satinaldehyde; canthoxal; vanillin; ethyl vanillin; cinnamic aldehyde; cis-4-decenal; trans-4-decenal; cis-7-decenal; undecylenic aldehyde; trans-2-hexenal; trans-2-octenal; 2-undecenal; 2,4-dodecadeienal; cis-4-heptenal; Florydral; cymal; butyl cinnamaldehyde; limonelal; amyl cinnamaldehyde; hexyl cinnamaldehyde; citronellal; citral; cis-3-hexen-1-al; and mixtures thereof; more preferably wherein at least one of the first monovalent moiety and the second monovalent moiety is an organic group comprising from about 8 to about 18 chain atoms, even more preferably from about 10 to about 18 chain atoms, preferably wherein the chain atoms are carbon atoms.

L. The pro-benefit-agent compound according any of paragraphs A-K, wherein the benefit agent is an antimicrobial agent, preferably an antimicrobial agent selected from acetylacetone enolate, gossypol, nootkatone, or mixtures thereof, more preferably wherein at least one of the first monovalent moiety and the second monovalent moiety is an organic group comprising from about 6 to about 12 chain atoms, preferably wherein the chain atoms are carbon atoms.

M. The pro-benefit-agent compound according any of paragraphs A-L, wherein the pro-benefit agent compound is characterized by a structure according to Formula II:

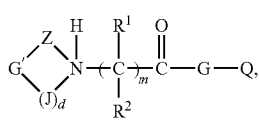

Formula II wherein the index m is selected from 1 to 6, preferably m is 1 or 2, more preferably m is 1; wherein the index d is selected from 1 to 3, preferably d is from 2 to 3, more preferably d is 2; wherein G and G' are each independently selected from —O—, —S—, or —N(R³)—, preferably wherein G is —O—, more preferably wherein G and G' are both —O—, wherein R³, if present, is selected from —H or a monovalent moiety with a molecular weight of from about 15 to about 142 Da, preferably wherein R³ is selected from —H or a monovalent moiety with a molecular weight from about 15 to about 30 Da, more preferably wherein R³ is —H; wherein Q comprises from 1 to 34 chain atoms, preferably from about 1 to about 18 chain atoms, more preferably from about 2 to about 14 chain atoms, most preferably wherein the chain atoms are carbon atoms; wherein R¹ and R² are independently selected from —H or a monovalent moiety with a molecular weight of from about 15 to about 1000 Da, preferably independently selected from —H or a monovalent moiety with a molecular weight of from about 15 to about 507 Da, more preferably independently selected from —H or a monovalent moiety with a molecular weight of from about 15 to about 142 Da; wherein Z is the benefit agent fragment, wherein each J is independently selected from the group consisting of C(R⁶)₂, —O—, and —N(R⁶)—, wherein each R⁶ is independently selected from H or a monovalent moiety with a molecular weight between 14 and 990 Da, more preferably R⁶ is selected from H or a monovalent moiety with a molecular weight between 14 and 186 Da, even more preferably R⁶ is H, with the proviso that a first R⁶ and a second R⁶ can optionally be taken together, where feasible, as a divalent substituent, preferably where the divalent substituent is selected from the group consisting of a fused ring, a spirocyclic ring, an unsaturated substituent, =N(R³), —O, and =S, wherein R³ is as defined above, and wherein at least one of the following is true: (a) at least one of Q and an R⁶, if present, comprises at least five, preferably at least eight, chain atoms, preferably carbon atoms, and/or (b) an R⁶ is present, and the sum of the number of chain atoms, preferably carbon chain atoms, in Q and the R⁶ is at least eight.

N. The pro-benefit-agent compound according to paragraph M, wherein Q comprises at least 8 chain atoms, and wherein no R⁶ group, if present, comprises more than 4 chain atoms, preferably no R⁶ group, if present, comprises more than 2 chain atoms, more preferably all the R⁶ groups, if present, are hydrogens.

O. The pro-benefit-agent compound according to paragraph M, wherein at least one R⁶ comprises at least 8 chain atoms, and wherein the Q group comprises from 1 to 4 chain atoms, preferably the Q group comprises from 1 to 2 chain atoms.

P. The pro-benefit-agent compound according any of paragraphs M-O, wherein at least one R¹ or R² group has the structure of a side chain of a proteinogenic amino acid, preferably the side chain of a proteinogenic amino acid selected from the group consisting of alanine, glycine, valine, phenylalanine, leucine, isoleucine, or combinations thereof, more preferably alanine, glycine, valine, phenylalanine, or combinations thereof, even more preferably alanine, glycine, or combinations thereof.

Q. The pro-benefit-agent compound according to any of paragraphs M-P, wherein the Z group is according to the following structure:

wherein "#" indicates the points of attachment to adjacent members of the heterocycle, wherein R⁴ is a monovalent organic moiety, wherein R⁵ is —H or a monovalent organic moiety, with the proviso that R⁴ and R⁵ may be taken together to form a cyclic moiety, wherein when the bonds marked by "#" are broken, the pro-benefit-agent compound releases a benefit agent according to the structure R⁵—C(O)—R⁴.

R. The pro-benefit-agent compound according any of paragraphs A-Q, wherein the pro-benefit-agent compound is characterized by a structure according to Formula IV:

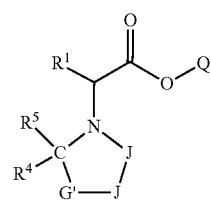

Formula IV wherein Q, R¹, R⁴, and R⁵, G', and J are as described above.

S. The pro-benefit-agent compound according any of paragraphs M-R, wherein the pro-benefit agent compound is characterized by a structure according to Formula V:

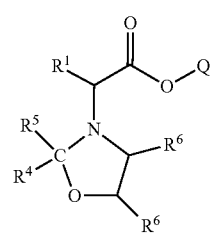

Formula V wherein Q, R¹, R⁴, R⁵, and R⁶ are as described above.

T. The pro-benefit agent compound according to any of paragraphs A-S, for Formula II: Q is an organic group comprising from about 8 to about 18 chain atoms, preferably wherein most or even all of the chain atoms are carbon atoms; G=—O—; m=1; $R^1$ has the structure of a side group of a proteinogenic amino acid; $R^2$ is —H; d=2; each J=C $(R^6)_2$, preferably wherein $R^6$ is hydrogen; G'=—O—; Z is a fragment of a perfume raw material, preferably a perfume raw material that comprises an aldehyde moiety.

U. The pro-benefit-agent compound according any of paragraphs A-T, wherein the pro-benefit agent further comprises a second benefit agent fragment, preferably wherein the pro-benefit-agent compound is characterized by a structure according to Formula II, and the second benefit agent fragment is part of a group consisting of Q, $R^1$, $R^2$, or $R^6$.

V. A treatment composition comprising an adjunct ingredient and the pro-benefit-agent compound according to any of paragraphs A-U.

W. The treatment composition according to paragraph V, wherein the adjunct ingredient comprises one or more of the following: surfactants, conditioning actives, deposition aids, rheology modifiers or structurants, bleach systems, antioxidants, stabilizers, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, silicones, hueing agents, aesthetic dyes, neat perfume, perfume delivery systems, structure elasticizing agents, carriers, hydrotropes, processing aids, anti-agglomeration agents, coatings, formaldehyde scavengers, and/or pigments.

X. The treatment composition according any of paragraphs V or W, wherein the adjunct ingredient comprises a conditioning active, preferably wherein the conditioning active comprises quaternary ammonium ester compounds, more preferably wherein the quaternary ammonium ester compounds are present at a level of from about 2 wt % to about 35 wt %, preferably from about 4 wt % to about 25 wt %, more preferably from about 5 wt % to about 20 wt %, preferably from about 6 wt % to about 15 wt %, more preferably from about 7 wt % to about 12 wt %, by weight of the treatment composition.

Y. The treatment composition according any of paragraphs V-X, wherein the treatment composition further comprises neat perfume, preferably neat perfume that comprises an alcohol-containing perfume raw material.

Z. The treatment composition according any of paragraphs V-Y, wherein the treatment composition is a consumer product, preferably a consumer product selected from a fabric care composition, a hard surface cleaner composition, a dish care composition, a hair care composition, a body cleansing composition, or a mixture thereof.

AA. The treatment composition according any of paragraphs V-Z, wherein the treatment composition is in the form of a liquid composition, a granular composition, a hydrocolloid, a single-compartment pouch, a multi-compartment pouch, a dissolvable sheet, a pastille or bead, a fibrous article, a tablet, a stick, a bar, a flake, a foam or mousse, a non-woven sheet, or a mixture thereof.

BB. The treatment composition according any of paragraphs V-AA, wherein the pro-benefit-agent compound is present in the treatment composition at a level of from about 0.001% to about 30%, by weight of the treatment composition.

CC. A pro-benefit-agent precursor compound, wherein the precursor compound is characterized by a structure according to Formula VII:

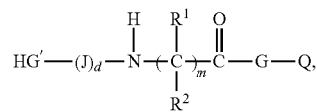

Formula VII wherein the groups and indices are as defined above.

DD. A premix composition comprising: a pro-benefit-agent precursor compound, wherein the precursor compound is characterized by a structure according to Formula VII:

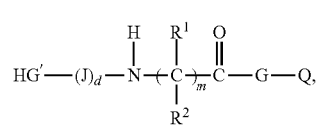

Formula VII wherein the groups and indices are as defined above; and a benefit agent, the benefit agent comprising an aldehyde moiety, a ketone moiety, or combinations thereof; wherein the pro-benefit-agent precursor compound and the benefit agent may optionally react to form a pro-benefit agent compound according any of paragraphs A-U, wherein the sum of the weight percents of the pro-benefit-agent precursor compound, the benefit agent, and the pro-benefit-agent compound, if present, is from about 10% to about 100%, preferably from about 25% to about 100%, more preferably from about 50% to about 100%, even more preferably from about 75% to about 100%, by weight of the premix composition.

EE1. The premix composition according to paragraph DD, wherein the premix composition further comprises water, preferably wherein the premix composition is in the form of an emulsion, more preferably an oil-in-water emulsion.

EE2. The premix composition according to paragraph DD, wherein the premix composition comprises less than about 10%, preferably less than 5%, more preferably less than 1%, even more preferably less than 0.1% water, by weight of the premix composition.

FF. The premix composition according any of paragraphs DD or EE, wherein the molar ratio of the pro-benefit-agent precursor compound and the benefit agent is from about 3:1 to about 1:3, preferably from about 2:1 to about 1:2, more preferably from about 1.5:1 to about 1:1.5, more preferably from about 1.2:1 to about 1:1.2, even more preferably from about 1:1.

GG. A method of making a treatment composition according any of paragraphs V-BB, wherein the method comprises at least one of the following: (a) combining a pro-benefit-agent compound with an adjunct ingredient, preferably wherein the adjunct ingredient is part of a base composition; (b) combining a premix composition according any of paragraphs DD-FF with an adjunct ingredient, preferably wherein the adjunct ingredient is part of a base composition; (c) combining a pro-benefit-agent precursor compound, a benefit agent, and an adjunct ingredient, preferably wherein the adjunct ingredient is part of a base composition and the pro-benefit-agent precursor compound and the benefit agent are each added to the base composition as separate inputs.

HH. A method of treating an article or a surface, wherein the method comprises treating the article or surface with a treatment composition according to any of claims V-BB, optionally in the presence of water, optionally further including the step of rinsing and/or drying the article or surface.

Test Methods

Preparation of a Premix Fluid (e.g., Nil-Water)

A premix fluid may be prepared as follows.

Method A: A benefit agent that comprises an aldehyde or ketone moiety is added in an approximately equal molar equivalent to the molar concentration of amine radicals present in a precursor compound (e.g., a precursor compound to Formula I above). This material is stirred with a magnetic stir bar at 150 rpm for at least 12 h.

Method B: A benefit agent that comprises an aldehyde or ketone moiety is added in an approximately equal molar equivalent to the molar concentration of amine radicals present in a precursor compound (e.g., a precursor compound to Formula VII above). This material is stirred with a magnetic stir bar at 150 rpm for at least 12 h in the presence of a water scavenger. The resulting fluid can either be mechanically filtered or directly added to a treatment composition.

As an illustrative example, 59 parts by weight of a modified amino acid as disclosed in Synthesis Example 3 below, is combined with 41 parts of a benefit agent (e.g., Cyclamen Aldehyde) using an IKA RW 20 D SI Mixer, Model RW20DS1, and IKA RI 342 impeller blade at 350 rpm.

Preparation of a Premix Emulsion (e.g., with Water)

A premix emulsion may be prepared as follows.

Method A: Starting with 1 part by weight of the premix fluid provided in the previous example, add diethylene glycol monobutyl ether (10.0 parts; ex TCI) and ECOSURF™ EH-9 (1 part; ex The Dow Chemical Company). The mixture is added to a Flacktek DA150.FVZ-K speed mixer for 1 min at 3,500 rpm. Water (88 parts in total) is added in two equal, separate additions; after each water addition, the mixture is mixed with the a Flacktek DA150.FVZ-K speed mixer at 3,500 rpm for 10-15 min.

Method B: Starting with 1 part by weight of the precursor compound (e.g., a hydrophobically modified amino acid), add diethylene glycol monobutyl ether (10.0 parts; ex TCI) and ECOSURF™ EH-9 (1 part; ex The Dow Chemical Company). The mixture is added to a Flacktek DA150.FVZ-K speed mixer for 1 min at 3,500 rpm. Water (88 parts in total) is added in two equal, separate additions; after each water addition, the mixture is mixed with the a Flacktek DA150.FVZ-K speed mixer at 3,500 rpm for 10-15 min. A benefit agent is added in an approximately equal molar equivalent to the molar concentration of amine radicals present in the precursor compound.

As an illustrative example, 99 parts by weight of an emulsified fluid containing a modified amino acid (which includes about 1 part by weight of the modified amino acid) as disclosed in Synthesis Example 3 below, emulsified as described above, is combined with 1 part of a benefit agent (e.g., cyclamen aldehyde).

Preparation of a Test Fabric Enhancer/Softener Composition

A 7.5 wt % N,N-di(tallowoyloxyethyl)-N,N-dimethylammonium chloride in water mixture is provided. A premix fluid as described above, a premix emulsion as described above, or two discrete neat fluids (one being the pro-benefit-agent precursor, such as a modified amino acid; the other being the benefit agent, such as one or more perfume raw materials) are added in an amount such that the concentration of the benefit agent or benefit material fragment in the fabric softener is about 0.3 wt % of the final fabric softener composition. The mixture is stirred for 5 min with an IKA RW 20 D SI Mixer, Model RW20DS1, and IKA RI 342 impeller blade at 350 rpm. A structurant and a deposition aid is added, and the mixture is stirred for 10 min. Water is added if needed to standardize the concentration of N,N di(tallowoyloxyethyl)-N,N dimethylammonium chloride amongst test legs to 7.3 wt %, and the mixture stirred for 5 min. The pH is adjusted to 2-3 with HCl, if necessary.

Preparation of a Test Pastille Composition

A mixture of 98.01 parts by weight of molten PEG-8000 material and 0.59 parts by weight of the pro-benefit-agent premix fluid of Synthetic Example 1 is added in a speed mixer cup. The speed mixer cup is quickly placed in a Flacktek DA150.FVZ-K speed mixer for 1 min at 3500 rpm. Sample pastilles are immediately made from the mixture by pouring into blue siliconized rubber molds that are pre-equilibrated to 4° ° C. and spread with a 10" plastic taping knife. The pastilles are cooled at room temperature for approximately 30 min, then the pastilles are removed from the mold and stored under ambient conditions.

Preparation of a Test Fabric Detergent Composition

To 97.58 parts by weight of TIDE Original Scent liquid detergent is added 2.42 parts by weight of the pro-benefit-agent-compound premix fluid of Synthetic Example 3B. The amount is selected such that the concentration of the selected benefit agent or benefit material fragment in the final detergent is about 1 wt % after the fabric treatment composition. The mixture is stirred for 10 min with an IKA RW 20 D SI Mixer, Model RW20DS1, and IKA RI 342 impeller blade at 350 rpm.

Preparation of a Dishwashing Liquid Detergent 0.6 parts by weight of a pro-benefit-agent compound premix fluid are added to 99.4 parts by weight of Ultra Dawn Blue Dishwashing Liquid. The pro-benefit-agent amino acid ester is added in an amount such that the concentration of the benefit agent or benefit material fragment in the dishwashing liquid is about 0.2 wt % after composition. The mixture is mixed for 1 hour on a Thermo Scientific Tube Roller, Model No. 88881003, and at 80 rpm.

Fabric Preparation Method

To prepare fabrics for Headspace analysis testing, fabric samples (100% Cotton Terry Cloth, Item Number ITL 1022-15PGP, CalderonTextiles, Inc. 6131 W. 80tA St., Indianapolis, Ind. 46278, Desized and conditioned with 3 wash cycles of Detergent and Fabric Softener) are treated with the detergents or fabric conditioners in a manner consistent with North American consumers via clothes mini-washing machines, full scale machines, and clothes dryers. Fabric are equilibrated at 21.1° C. and 50% relative humidity for 24 hours, unless noted otherwise, prior to Headspace GCMS analysis (see methods below). Ballast loads are comprised of cotton and polycotton knit swatches approximately 20×20 inches (50×50 cm) in size.

Wash Treatment Conditions

In the fabric enhancer/softener compositions performance tests below, the fabrics are treated with the following wash treatment conditions: Wash: 12 min agitation, 30.6° C. Rinse: 2 min agitation, 15.5° C. Water Hardness: 137 ppm. Water: 7.6 pH. Fabric Load Weight: 290 g. Tumble Dry Setting: 50 min High, Cotton. Detergent Dose: 9.65 g. Fabric Softener Dose: 5.71 g.

In the pastille composition performance tests below, the fabrics are treated with the following wash treatment conditions: North America Kenmore 600 Series top-loading washing machines are used. Each machine is set to run a Normal single cycle including a 12-minute wash agitation period, and 1 three-minute rinse. The water used is 137 ppm hardness and 30.6° C. for the wash, and 15.5 °C for the rinse. The water volume at each step is 64 Liters. The total fabric load weight is 3.6 kg (which included 32 test fabric hand towel terry cloths, 9 of 100% cotton ballast, and about 5 of 50/50 polycotton ballast). The detergent used is TIDE Original Scent liquid without perfume (produced by The Procter & Gamble Company). Detergent is dosed at 81 g into the wash water while the wash water is filling. After the detergent is added, 25 g of the pastilles being evaluated are also added, followed by the fabric load. After the water fill is complete, the machine enters the agitation period. This is followed by the wash agitation (Normal setting), and the rinse step (with corresponding spin cycle). After the wash process is completed, the fabrics are removed. The test fabrics are machine dried in Kenmore driers on Cotton/High setting, for 50 minutes or test fabrics are line-dried for 16 hours in a 21.1° C./50% relative humidity controlled room.

In the detergent composition performance tests below, the fabrics are treated with the following wash treatment conditions: Wash: 12 min agitation, 30.6° C. Rinse: 2 min agitation, 15.5° C. Water Hardness: 137 ppm. Water: 7.6 pH. Fabric Load Weight: 290 g. Tumble Dry Setting: 50 min High, Cotton. Detergent Dose: 9.65 g. Fabric Softener Dose: 5.71 g.

Headspace Analysis Above Fabrics

To determine the level of benefit agent material in the headspace above a fabric, the following procedure is used.

The following equipment is used: Gas Chromatograph 7890B equipped with a Mass Selective Detector (5977B) (MSD) and Chemstation quantitation package; Gerstel Multi-Purpose sampler equipped with a solid phase microextraction (SPME) probe or similar system; Divinylbenzene/Carboxen/Polydimethylsiloxane SPME fiber from Supleco part #57298-U (or similar fiber); 30 m×0.25 mm nominal diameter, 0.25 m film thickness, J&W 122-5532UI DB-5; 20 mL headspace vials.

To prepare the fabric for analysis, cut three 2.54 cm×5.08 cm cotton swatches from the cotton terry that is prepared and treated according to the above methods. Place each piece in a 20 mL headspace vial and cap.

The Gerstel auto sampler parameters are as follows: SPME—from Incubator; Incubation Temperature—65° C.; Incubation Time—10.00 min SAMPLE PARAMETERS; Vial Penetration—22.00 mm; Extraction Time—5.00 min; Ini. Penetration—54.00 mm; Desorption Time—300 s. The GC oven parameters are as follows for the Front SS Inlet He: Mode—Splitless; Heater—270° C.; GC Run Time—14.28 min. For the Oven: Initial temp.—40° C.; Hold Time—0.5 min; Heating Program—Rate of 17° C./min, Temp of 270° C., Hold Time of 0.25 min. The MSD parameters are as follows: Run in scan mode with a minimum range of 35 to 350 m/z.

Calibration curves are generated from the standards benefit agent material. Chemstation software (or similar quantitation software) calculates the mass amount in the headspace using the calibration curve for each perfume component.

Color Change of a Composition

A treatment composition may be tested for color changes according to the following procedure. The reflectance spectra and color measurements, including L*, a*, and b* were made using the LabScan XE reflectance spectrophotometer (HunterLabs, Reston, VA; D65 illumination, 10° observer, UV light excluded). L*, a* and b* values for treatment compositions are measured at time $t_{initial}$, i.e. start of test, after mixing in the benefit agent, and $t_{final}$, i.e. end of the stability test as defined in each experiment. The total color change ($\Delta E$) of a treatment composition is calculated based on the data collected at each time point t using the following equation:

$$\Delta E_t = [(L^*_c - L^*_s)^2 + (a^*_c - a^*_s)^2 + (b^*_c - b^*_s)^2]^{1/2}$$

wherein the subscripts c and s respectively refer to the control, i.e., the treatment composition with nil benefit agent, and the sample, i.e., the treatment composition with respective aldehyde/ketone benefit agent, where the values used to calculate $\Delta E_t$ are those at the corresponding time points $t_{initial}$ and $t_{final}$.

Samples were prepared by adding the pro-benefit-agent fluid premix (nil-water) to a base treatment composition with overhead mixing with a four blade IKA RW 20 impeller and gently mixed for 15 minutes. The treatment composition is placed into a 50 mL (25 cm$^2$) CELLSTAR® cell culture flask with standard screw cap. At $t_{initial}$ and after $t_{final}$ at the specified temperature, color appearance of each treatment composition sample is measured on a LabScan XE 10 reflectance spectrophotometer (HunterLabs, Reston, VA; D65 illumination, 10° observer, UV light excluded).

HLB Value of Nonionic Surfactants

Nonionic surfactants can be classified by the balance between the hydrophilic and lipophilic moieties in the surfactant molecule. The hydrophile-lipophile balance (HLB) scale devised by Griffin in 1949 is a scale from 0-20 (20 being Hydrophilic) used to characterize the nature of surfactants. The HLB of a surfactant may be calculated as follows:

$$HLB = 20 * Mh/M$$

where Mh is the molecular of the hydrophilic portion of the molecule, and M is the molecular mass of the whole molecule, giving a result on a scale of 0 to 20. An HLB value of 0 corresponds to a completely lipophilic/hydrophobic molecule, and a value of 20 corresponds to a completely hydrophilic/lipophobic molecule. See Griffin, W. C. Calculation of HLB values of Nonionic Surfactants, J. Soc. Cosmet. Chem. 1954, 5, 249-256. The HLB values for commonly-used surfactants are readily available in the literature (e.g., HLB Index in Mccutcheon's Emulsifiers and Detergents, MC Publishing Co., 2004). The HLB value for a mixture of surfactants can be calculated as a weighted average of the HLB values of the surfactants.

Test Method for Determining Log P

The value of the log of the Octanol/Water Partition Coefficient (log P) is computed for a material (such as the alcohol version of a hydrophobe/Q group, or of a PRM) as described here.

The log P of an individual material is calculated using the Consensus log P Computational Model, version 14.5 (Linux) available from Advanced Chemistry Development Inc. (ACD/Labs) (Toronto, Canada) to provide the unitless log P value. The ACD/Labs' Consensus log P Computational Model is part of the ACD/Labs model suite.

EXAMPLES

The examples provided below are intended to be illustrative in nature and are not intended to be limiting.

Synthesis Examples

The following Synthetic Examples 1-7 exemplify the synthesis of illustrative pro-benefit-agent compounds (e.g., Synthetic Example 1) and their alkanolamine-containing precursors (e.g., Synthetic Example 1'), according to the present disclosure.

Comparative Synthetic Example A shows a comparative modified amino acid ester. Comparative Synthetic Example A interacts with aldehydes through an imine moiety, which is chemically distinct to the heterocyclic-forming materials described herein.

For consistency and illustrative/comparative purposes, each example reacts a different neat pro-benefit-agent precursor compound with the same perfume raw material, precyclemone B (containing a quaternary alpha carbon aldehyde moiety), which has the structure provided below. As additional examples, Synthetic Examples 2B, 3, and 4 form pro-benefit-agent compounds with cyclamen aldehyde, which contains a tertiary alpha carbon aldehyde moiety. The structures of the PRMs are provided below:

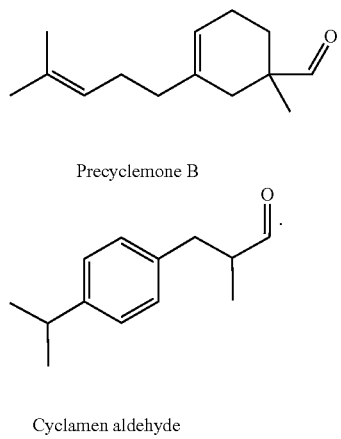

Precyclemone B

Cyclamen aldehyde

However, it is understood that other aldehyde- or ketone-containing benefit agents according to the present disclosure may also lead to the formation of suitable pro-benefit-agent compounds; some of these are exemplified and tested in the Performance Examples below.

It is also understood that the Synthetic Examples may be formulated into a treatment composition as a liquid premix emulsion or as a neat fluid or as a liquid premix fluid as described above; however, for the case of the reported performance and stability examples below, all Synthetic Examples are assumed to be formulated directly as liquid premix fluids into the treatment composition unless indicated otherwise.

For each Synthetic Example, the resulting pro-benefit-agent compound (e.g., a modified alkanolamine amino acid ester molecule) is illustrated with precyclemone B (or in the case of Synthetic Examples 2B, 3, and 4—cyclamen aldehyde) and provided below in Table D. Comparative Synthetic Example A, a modified amino acid ester, is exemplified with cinnamic aldehyde in Table D, although it does not contain the heterocyclic forming pro-benefit modified amino acid ester.

Methods of Preparing Pro-Benefit-Agent Compounds (e.g., Modified Amino Acid Esters)

In the following synthesis examples, the materials are generally obtained/available from Sigma-Aldrich (St. Louis, MO, USA), except as indicated below. The amino acids are generally provided at >98% or even >99% purity. The alcohols are generally provided at >97%, >98%, or even >99% purity. Cyclamen aldehyde and cinnamic aldehyde (ex Sigma-Aldrich) is provided at >95% purity. Precyclemone B is available from IFF of New York, NY.

General Method A: General Preparation of Amino Acid Ester Precursor Compound

To prepare an amino acid ester compound from an amino acid and an alkyl alcohol, a round bottom flask is charged with 1 equiv. of a free base amino acid starting material. One (1) equiv. of a selected alcohol reagent is added to the flask, followed by the addition of 1.2 equiv. of p-Toluene-sulfonic acid monohydrate (PTSA). The materials in the flask are then diluted with toluene and refluxed for 12 h using a dean-stark apparatus. Toluene is then removed in vacuo, and the resulting crude material dissolved in chloroform. The solution is neutralized with $Et_3N$, washed 3× with $NaHCO_3$, and dried over anhydrous $MgSO_4$. Residual solvent is removed, and the washed material is diluted with cyclohexane and then stored at 0° C. for at least 12 h. The eluent is collected, yielding the desired modified amino acid ester.

General Method B: General Preparation of a Pro-Benefit-Agent Precursor Compound (e.g., Alkanolamine-Modified Amino Acid Esters)

A round bottom flask is charged with 1 equiv. of an amino acid ester precursor (as generally described in General Method A or from commercially available sources). To the flask is added 1.2 equiv. of the target oxirane material and 20 wt % of trifluoroethanol. The resulting mixture is refluxed for at least 8 h. Upon cooling, solvent is removed. The resulting material is then further purified by silica gel chromatography using a gradual 1:15 to 1:4 elution of EtOAc to hexane (V/V).

General Method C: General Preparation of Pro-Benefit-Agent Compound

A round bottom flask is charged with 1 equiv. of the alkanolamine-modified amino acid precursor (e.g., as generally described in General Method B). To the flask is added 1 equiv. of either cyclamen aldehyde or precyclemone B. To the fluid is added 20 wt % 4 Å molecular sieves, and the mixture stirred for 12 h. The resulting mixture is filtered using a Pyrex 36060-30M Brand 36060 fritted funnel and used directly.

Comparative Synthetic Example A*

Comparative Synthetic Example A'* was prepared as described in General Method A, but using 10.0 g of L-Valine, 16.1 g of 1-dodecanol, and 19.5 g PTSA $H_2O$. The isolated fluid of Synthetic Example A'* was then mixed with cinnamic aldehyde as described in General Method C, but where the alkanolamine amino acid precursor is substituted with the amino acid ester precursor obtained from General Method A; the reaction yields Comparative Synthetic Example A*. The independent fluid A* appears stable for several months by $^1H$ NMR.

Synthetic Example 1

The first step was performed as described in General Method A, but using 10.0 g of L-Valine, 23.1 g of 1-Octadecanol, and 19.5 g PTSA $H_2O$. Synthetic Example 1' was then prepared as described in General Method B, but using the material obtained in the first step and 1.2 equiv. of propylene oxide. The isolated precursor Synthetic Example 1' was then mixed with precyclemone B (IFF New York, NY) as described in General Method C, yielding Synthetic Example 1. The colorless independent fluid 1 appears stable for several months by $^1H$ NMR.

Synthetic Example 2A

To a solution of 10 g of L-Valine ethyl ester hydrochloride (Sigma Aldrich, St. Louis, MO, USA) in 2.2 g of trifluoroethanol is added 1 equiv. of $Et_3N$. Synthetic Example 2' was then prepared as described in General Method B, but using 1.2 equiv. of 1,2-epoxydodecane. The isolated precursor Synthetic Example 2' was then mixed with precyclemone B (IFF New York, NY) as described in General Method C, yielding Synthetic Example 2A. The colorless independent fluid 2A appears stable for several months by $^1H$ NMR.

Synthetic Example 2B

To a solution of 10 g of L-Valine ethyl ester hydrochloride (Sigma Aldrich, St. Louis, MO, USA) in 2.2 g of trifluoroethanol is added 1 equiv. of $Et_3N$. Synthetic Example 2' was then prepared as described in General Method B, but using 1.2 equiv. of 1,2-epoxydodecane. The isolated precursor Synthetic Example 2' was then mixed with cyclamen aldehyde (Sigma Aldrich, St. Louis, MO, USA) as described in General Method C, yielding Synthetic Example 2B. The colorless independent fluid 2B appears stable for several months by $^1H$ NMR.

Synthetic Example 3

The first step was performed as described in General Method A, but using 10.0 g of L-Valine, 16.1 g of 1-Dodecanol, and 19.5 g PTSA $H_2O$. Synthetic Example 3' was then prepared as described in General Method B, but using the material obtained in the first step and 1.2 equiv. of butyl glycidyl ether. The isolated precursor Synthetic Example 3' was then mixed with cyclamen aldehyde (Sigma Aldrich, St. Louis, MO, USA) as described in General Method C, yielding Synthetic Example 3. The colorless independent fluid 3 appears stable for several months by $^1H$ NMR.

Synthetic Example 4

The first step was performed as described in General Method A, but using 10.0 g of L-Valine, 16.1 g of 1-Dodecanol, and 19.5 g PTSA $H_2O$. Synthetic Example 4' was then prepared as described in General Method B, but using the material obtained in the first step and 1.2 equiv. of propylene oxide. The isolated precursor Synthetic Example 4' was then mixed with cyclamen aldehyde (Sigma Aldrich, St. Louis, MO, USA) as described in General Method C, yielding Synthetic Example 4. The colorless independent fluid 4 appears stable for several months by $^1H$ NMR.

Synthetic Example 5

To a solution of 10 g of L-Alanine ethyl ester hydrochloride (Sigma Aldrich, St. Louis, MO, USA) in 2.2 g of trifluoroethanol is added 1 equiv. of $Et_3N$. Synthetic Example 5' was then prepared as described in General Method B, but using 1.2 equiv. of 1,2-epoxydodecane. The isolated precursor Synthetic Example 5' was then mixed with precyclemone B (IFF New York, NY) as described in General Method C, yielding Synthetic Example 5. The colorless independent fluid 5 appears stable for several months by $^1H$ NMR.

Synthetic Example 6

The first step was performed as described in General Method A, but using 10.0 g of L-Valine, 11.1 g of 1-Octanol, and 19.5 g PTSA $H_2O$. Synthetic Example 6' was then prepared as described in General Method B, but using the material obtained in the first step and 1.2 equiv. of Butyl glycidyl ether. The isolated precursor Synthetic Example 6' was then mixed with precyclemone B (IFF New York, NY) as described in General Method C, yielding Synthetic Example 6. The colorless independent fluid 6 appears stable for several months by 1H NMR.

Synthetic Example 7

The first step was performed as described in General Method A, but using 10.0 g of L-Valine, 11.1 g of 1-Octanol, and 19.5 g PTSA $H_2O$. Synthetic Example 7' was then prepared as described in General Method B, but using the material obtained in the first step and 1.2 equiv. of propylene oxide. The isolated precursor Synthetic Example 7' was then mixed with precyclemone B (IFF New York, NY) as described in General Method C, yielding Synthetic Example 7. The colorless independent fluid 7 appears stable for several months by $^1H$ NMR.

Structures of the Synthetic Examples

Table D below illustrates the structures of the Synthetic Examples 1-7, as well as their precursor compounds (denoted with a "'").

Table D also includes Comparative Synthetic Example A* as the precursor, and the modified amino acid ester that includes an imine bond Comparative Synthetic Example A*. The comparative examples are marked with an asterisk (*).

TABLE D

| Structural representation of the Synthesis Examples ||||
| --- | --- | --- | --- |
| No. | Precursor Compound (e.g., before the addition of a benefit agent) | No. | Pro-Benefit-Agent Compound (e.g., a compound according to Formula I, not including Comparative Example A*) |
| A'* | 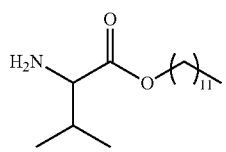 | A* | 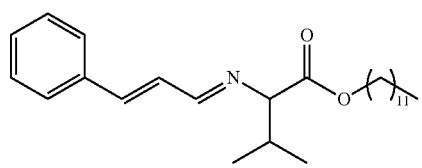 |

TABLE D-continued
Structural representation of the Synthesis Examples
| No. | Precursor Compound (e.g., before the addition of a benefit agent) | No. | Pro-Benefit-Agent Compound (e.g., a compound according to Formula I, not including Comparative Example A*) |
|---|---|---|---|
| 1' | 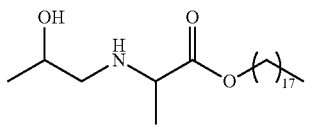 | 1 | 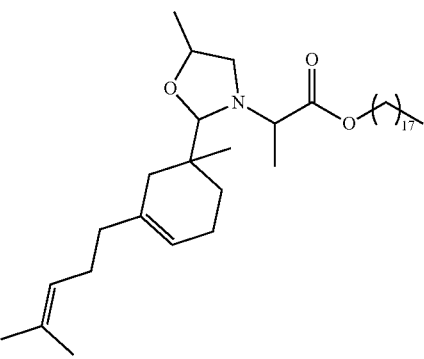 |
| 2' | 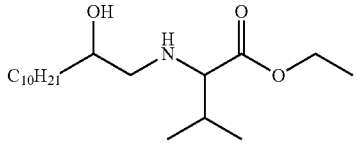 | 2A | 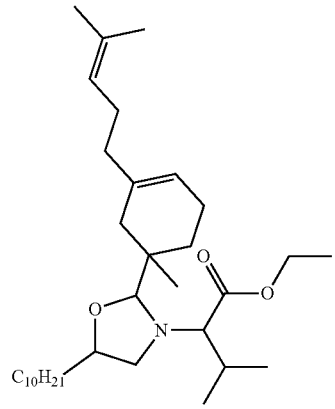 |
|  |  | 2B | 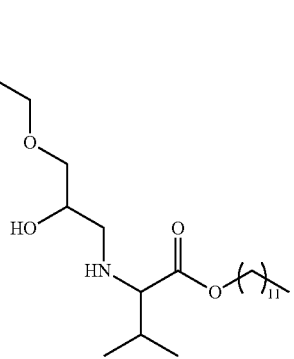 |
| 3' | 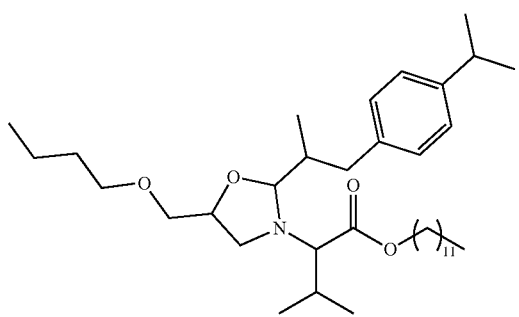 | 3 |  |

TABLE D-continued

Structural representation of the Synthesis Examples

| No. | Precursor Compound (e.g., before the addition of a benefit agent) | No. | Pro-Benefit-Agent Compound (e.g., a compound according to Formula I, not including Comparative Example A*) |
|---|---|---|---|
| 4' | 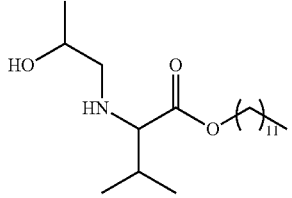 | 4 | 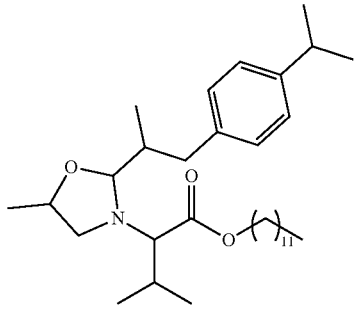 |
| 5' | 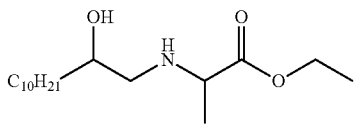 | 5 | 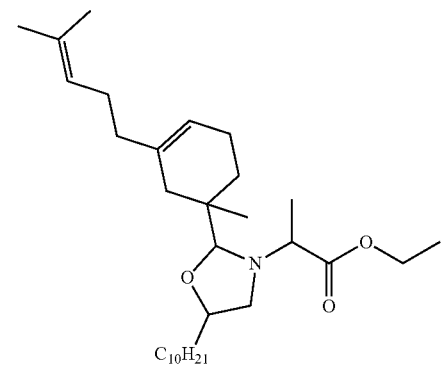 |
| 6' | 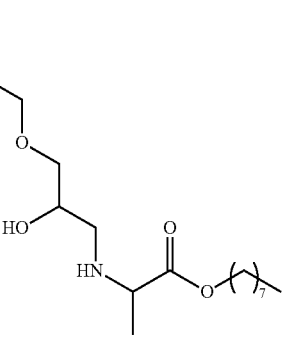 | 6 | 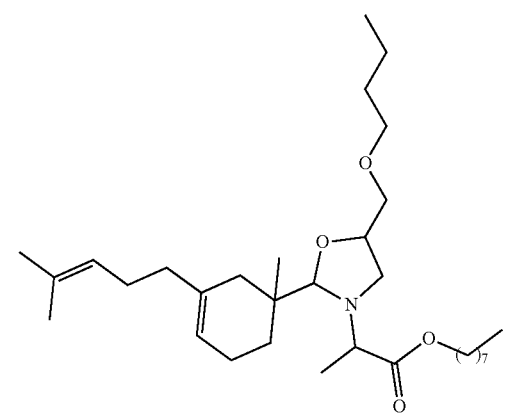 |
| 7' | 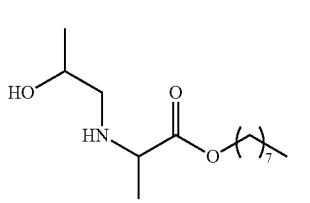 | 7 | 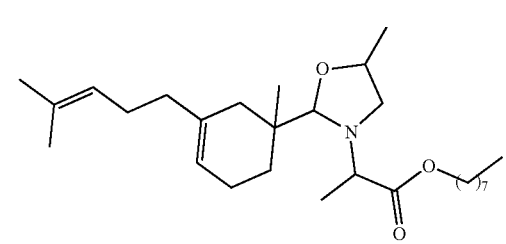 |

In the following Performance Examples and Stability Examples, heterocyclic pro-benefit-agent precursor compounds (e.g., alkanolamine-modified amino acid ester molecules) and the indicated perfume raw materials are mixed substantially following a procedure aligned with the method found in the Test Methods section above ("Preparation of a Premix Fluid"). Despite the different methods of preparation between the single PRM fragments of Synthesis Examples and the Performance and Stability Examples, the inputs and outputs, in terms of the heterocyclic pro-benefit-agent compounds, are substantially the same.

Performance Examples

In Performance Examples 1-4 below, treatment compositions comprising neat perfume oil, or a heterocyclic pro-benefit-agent compounds according to the present disclosure (e.g., based on alkanolamine modified amino acid esters), or premix emulsions comprising comparative modified amino acid esters are compared via treatment cycles in an automatic washing machine according to the Fabric Treatment methods provided above. After treatment, the fabrics are tested for Headspace Analysis according to the test methods provided above. The data below shows the benefits afforded by hydrophobically-modified amino acid esters, and their interaction with benefit agents through heterocycles, in delivering benefit agents.

Performance Example 1. Benefits in a Dry Particle Formulation

Initially, Synthetic Example 1' is reacted with an aldehyde accord as described above leading to similar structures to Synthetic Example 1, but where the fragment of Precyclemone B is replaced with the fragments of the added aldehyde accord. In this example, the formulation of material is prepared in a dry-formed particles application (e.g., a pastille comprising polyethylene glycol as a carrier; similar in size and shape to those sold as DOWNY UNSTOPABLES™ by The Procter & Gamble Company). The formulations of the particles for each leg are provided in Table 1A, where Synthetic Example 1 is introduced as a premix fluid as detailed above. Amounts are provided by % weight of the composition.

TABLE 1A

| Leg | PEG-8000 | Modified Amino Acid Premix Fluid | Neat PRMs |
| --- | --- | --- | --- |
| Neat raw materials[a] | 99.34% | 0.00% | 0.66% |
| Synthetic Example 1[a] | 98.01% | 1.99% | 0.00% |

[a]The cumulative raw materials equated 0.66 wt % of aldehyde accord. The formulation of the accord is composed as follows: 10 wt % Methyl nonyl acetaldehyde, 40 wt % P.T. Bucinal, 20 wt % Precyclemone B, and 30 wt % Floralozone.

In the example below, the premix materials of Synthetic Example 1 are provided to a Test Fabric Pastille Composition, prepared as provided in the Test Methods above. Test fabrics are prepared, wash treated, and tested for headspace analysis above the dry fabrics according to the Test Methods above. The performance test results are provided in Table 1B.

TABLE 1B

Average headspace concentration of aldehyde benefit agent[a] above fabrics

| Compound | Amount of Methyl Nonyl Acetaldehyde released (nmol/L) | Amount of Floralozone released (nmol/L) | Amount of P.T. Bucinal released (nmol/L) | Amount of Precyclemone B released (nmol/L) | Total Headspace Amount released (nmol/L) |
| --- | --- | --- | --- | --- | --- |
| Neat Raw Materials | 0.42 | 0.02 | 0.11 | 0.22 | 0.77 |
| Synthetic Example 1 | 0.71 | 0.04 | 0.19 | 0.42 | 1.36 |

[a]The cumulative raw materials equated 0.66 wt % of aldehyde accord. The formulation of the accord is composed as follows: 10 wt % Methyl nonyl acetaldehyde, 40 wt % P.T. Bucinal, 20 wt % Precyclemone B, and 30 wt % Floralozone.

As shown in Table 1B, the Synthetic Example 1 in a dry particle formulation shows an advantage over the neat raw materials through the rinse and dryer.

Performance Example 2. Benefits in a Liquid Fabric Enhancer Formulation

The heterocyclic pro-benefit modified amino acid material Synthetic Example 2A, was examined in a liquid fabric enhancer formulation. In the example below, equal molar concentrations of aldehydic benefit agent, described in the respective test legs, are provided to a precursor alkanolamine amino acid as describe above, then formulated into a Test Fabric Enhancer/Softener Composition, prepared as provided in the test methods above. Test fabrics are prepared, wash treated, and tested for headspace analysis above the fabrics according to the test methods above.

Results of the Headspace Analysis Above Fabrics testing are provided below in Table 2A.

TABLE 2A

Average headspace concentration of Precyclemone B[a] above fabrics

| Compound | Amount of Precyclemone B released (nmol/L) |
| --- | --- |
| Neat Raw Materials | 2.82 |
| Synthetic Example 2A | 5.65 |

[a]The benefit formulation is at 0.2 wt % of Precyclemone B.

As shown in Table 2A, the heterocyclic forming modified amino acid esters 2A delivered an improvement in total headspace over the neat raw materials.

Performance Example 3. Effect of Monovalent Moieties

To further evaluate these materials, a sterically less-encumbered aldehyde material was examined. In the examples below, equal molar concentrations of cyclamen aldehyde, described in the respective test legs, are provided to a alkanolamine precursor amino acid, Synthetic Examples 2B, 3, and 4 as describe above, then formulated into a Test Fabric Enhancer/Softener Composition, prepared as provided in the test methods above.

For convenience, the structures of the first monovalent moiety (i.e., that which is attached at the core's carbonyl moiety; a Q group) and second monovalent moiety (i.e., that which is attached to the heterocyclic moiety; an $R^6$ group) of each are provided below in Table 3A. In the structures provided below, the symbol "#" indicates the point of respective attachment.

TABLE 3A

| Synthetic Example | First monovalent moiety (Q) (total chain atoms/total chain carbons) | Second monovalent moiety ($R^6$) (total chain atoms/total chain carbons) |
| --- | --- | --- |
| 2B | #—CH$_2$—CH$_3$ (2/2) | #—C$_{10}$H$_{21}$ (10/10) |
| 3 | #—(CH$_2$)$_{11}$—CH$_3$ (12/12) | #—CH$_2$—O—(CH$_2$)$_3$—CH$_3$ (6/5) |
| 4 | #—(CH$_2$)$_{11}$—CH$_3$ (12/12) | #—CH$_3$ (1) |

Test fabrics are prepared, wash treated, and tested for headspace analysis above the fabrics according to the test methods above. Results of the Headspace Analysis Above Fabrics testing are provided below in Table 3B.

TABLE 3B

Average headspace concentration of Cyclamen aldehyde[a] above fabrics

| Compound | Amount of Cyclamen aldehyde released (nmol/L) |
| --- | --- |
| Neat Raw Materials | 1.440 |
| Synthetic Example 2B | 6.257 |
| Synthetic Example 3 | 4.158 |
| Synthetic Example 4 | 1.930 |

[a]The benefit formulation is at 0.2 wt % of Cyclamen aldehyde.

As shown in Table 3, the alkanolamine-modified amino acid esters 2B, 3, and 4 delivered an improvement in total headspace over neat raw materials.

The dodecyl ester amino acid materials 3 and 4 are only distinct by the substitution on the heterocyclic ring. The glycidyl ether construct 3, which is relatively more electron-deficient, delivered a higher headspace of Cyclamen aldehyde through the wash.

Additionally, comparison of 3, with synthetic example 2B suggests that a shorter ester attached to the core in combination with a longer hydrophobe on the heterocycle ring is the most preferred substitution pattern. Synthetic example 2B, based on the amino acid valine ethyl ester, had the highest total headspace among the series.

Performance Example 4. Comparison of Steric Hinderance (Including Different Amino Acid Side Groups)

The influence of steric hinderance of the amino acid side chain was examined in a liquid fabric formulation. In this example, various pro-benefit-agent compounds are examined.

In the example below, equal molar concentrations of aldehydic benefit agents, described in the respective test legs, are provided to alkanolamine precursor amino acids as describe above, then formulated into a Test Fabric Enhancer/Softener Composition, prepared as provided in the test methods above. Test fabrics are prepared, wash treated, and tested for headspace analysis above the fabrics according to the test methods above.

The (non-hydrogen) side group ($R^1$), first monovalent moieties (Q), and second monovalent moieties ($R^6$) for each tested compound are provided below in Table 4A. The symbol "#" indicates where the point of attachment at the relative position.

TABLE 4A

| Synthetic Example | Side Group (amino acid) | First Monovalent Moiety | Second Monovalent Moiety |
| --- | --- | --- | --- |
| 2B | #—CH(CH$_3$)—CH$_3$ (valine) | #—CH$_2$—CH$_3$ | #—C$_{10}$H$_{21}$ |
| 5 | #—CH$_3$ (alanine) | #—CH$_2$—CH$_3$ | #—C$_{10}$H$_{21}$ |
| 6 | #—CH$_3$ (alanine) | #—(CH$_2$)$_7$—CH$_3$ | #—CH$_2$—O—(CH$_2$)$_3$—CH$_3$ |
| 7 | #—CH$_3$ (alanine) | #—(CH$_2$)$_7$—CH$_3$ | #—CH$_3$ |

It is understood that for the rows reading "Synthetic Example 5," etc., both in Table 4B and in subsequent tables, the sample was prepared substantially in accordance with the method and precursor provided in the listed Synthetic Example, but with the benefit agent materials listed in the performance table (in equal molar concentrations to the precursor alkanolamine modified amino acid ester) rather than with just cyclamen aldehyde or precyclemone B, and formulated as a premix fluid as detailed above.

Results of the Headspace Analysis Above Fabrics testing are provided below in Table 4B.

TABLE 4B

Average headspace concentration of aldehyde benefit agents[a] above fabrics

| Compound | Amount of Methyl Nonyl Acetaldehyde released (nmol/L) | Amount of Floralozone released (nmol/L) | Amount of P.T. Bucinal released (nmol/L) | Amount of Precyclemone B released (nmol/L) | Total Headspace Amount released (nmol/L) |
| --- | --- | --- | --- | --- | --- |
| Neat Raw Materials | 0.36 | 0.14 | 1.09 | 0.18 | 1.77 |
| Synthetic Example 2 | 0.32 | 0.34 | 0.76 | 0.42 | 1.84 |
| Synthetic Example 5 | 1.24 | 0.41 | 2.62 | 0.79 | 5.05 |
| Synthetic Example 6 | 1.31 | 0.23 | 3.57 | 0.37 | 5.47 |
| Synthetic Example 7 | 0.72 | 0.51 | 3.17 | 0.41 | 4.80 |

[a]The cumulative raw materials equated 0.2 wt % of aldehyde accord. The formulation of the accord is composed as follows: 10 wt % Methyl nonyl acetaldehyde, 40 wt % P.T. Bucinal, 20 w t% Precyclemone B, and 30 wt % Floralozone.

As exemplified in this example heterocyclic modified alanine esters of Synthetic Examples 5, 6, and 7 delivered an improvement in total headspace over the neat raw materials and those based on valine ethyl esters (Synthetic Example 2). The improvement is particularly noted with aldehyde raw materials P. T. Bucinal and Methyl Nonyl Acetaldehyde in Synthetic Examples 5, 6, and 7. Without wishing to be bound by theory, it may be that steric repulsion between the amino acid side group and the substitution of the alpha carbon on the benefit agent may strongly influence performance.

As illustrated in the previous performance example, this test also suggests that the ethyl ester (Synthetic Example 5) and the glycidyl ether (Synthetic Example 6) amino acid constructs may be more preferred to Synthetic Example 7. This may be due to a difference in the hydrolysis rates based on the amount of hydrophobicity on the heterocyclic core, where hydrophobicity around the heterocyclic may be more preferred than hydrophobicity attached to the carbonyl-containing moiety of the amino acid esters.

Stability Example

In Stability Example 1, pro-benefit-agent compounds (e.g., modified amino acid esters) in premix fluids are formulated into treatment compositions, and the color stability is recorded upon storage.

Stability Example 1. Color Stability in a Liquid Treatment Composition

Premixes in fluid forms, comprising heterocyclic-forming pro-benefit-agent precursors (e.g. modified amino acid esters) and perfume raw materials, as well as related fabric softener products formed from such premix fluids are prepared. Color measurements of the fabric softener products that include the premix fluids (or neat PRMs) are measured as described in Test Methods above. Relatively lower $\Delta E_t$ values indicate relatively less color change compared to fresh product.

Aldehyde-containing benefit agents are formulated at 0.2 wt % of the overall treatment composition. The aldehydic perfume composition is as follows: 10 wt % Methyl nonyl acetaldehyde, 35 wt % P. T. Bucinal, 20 wt % Precyclemone B, 30 wt % Floralozone, and 5 wt % Cinnamic Aldehyde). As with previous examples, it is understood that the Synthetic Examples are made with the listed aldehydes rather than just cyclamen aldehyde or Precyclemone B, and reacted with the precursor compound (e.g., Synthetic Example 2') in the form of a premix fluid as detailed above. Comparative compositions are made with a modified amino acid ester and the same aldehydes as described above (e.g., Comparative Example A*).

Color stability of the fabric softener products upon storage for one week is assessed by the Color Change of a Composition test method provided above. The results are provided in Table S1 below.

As shown in Table S1, a product formulated with Synthetic Example 2, which contains a heterocyclic-forming modified amino acid ester in combination with the benefit agent fragment, demonstrates similar $\Delta E_t$ to a product formed with neat raw materials.

Further, a product formulated with Synthetic Example 2 demonstrates relatively lower $\Delta E_t$ after storage at 50° C. compared to the product formulated with the imine-containing modified amino acid ester of Competitive Synthetic Example A*. Without wishing to be bound by theory, it is believed that π-bonds are likely the origin of color intensity for imines represented in Comparative Synthetic Example A*. The influence of π-bond conjugation is further highlighted using cinnamic aldehyde, where the extended conjugation upon imine formation leads to visible wavelength coloring. Additionally or alternatively, it is believed the nature of bonding in heterocycles precludes static π-bonds, resulting in the heterocyclic moieties of Synthetic Examples 2 yielding improved color stability with time due to reduced conjugation and diminished condensation side reactions.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

TABLE S1

Average ($\Delta E_t{}^a$) absorption change upon storing for 1 week.

| Compound | $\Delta E_t$ [L*, a*, b*] Temperature storage at 50° C. | $\Delta E_t$ [L*, a*, b*] Temperature storage at 5° C. | [L*, a*, b*] Fresh Sample |
|---|---|---|---|
| Neat Raw Materials | 1.30 [73.63, −3.07, −6.41] | 0.33 [72.54, −2.34, −6.34] | [72.63, −2.34, −6.02] |
| Comp. Synthetic Example A* | 10.95 [66.57, 1.19, 2.56] | 1.93 [72.81, −2.8, −3.93] | [72.65, −2.41, −5.81] |
| Synthetic Example 2 | 1.51 [72.42, −3.33, −6.29] | 0.82 [72.74, −2.4, −6.15] | [73.3, −2.35, −5.55] |

$^a\Delta E_t$ is calculated as defined in test methods.

What is claimed is:

1. A treatment composition comprising an adjunct ingredient and a pro-benefit-agent compound,
wherein the pro-benefit agent compound is characterized by a structure according to Formula II:

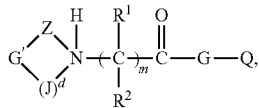

Formula II wherein the index m is 1,
wherein the index d is 2,
wherein G and G' are —O—,
wherein $R^3$, if present, is selected from —H or a monovalent moiety with a molecular weight of from about 15 to about 142 Da;
wherein Q is an organic group comprising from about 8 to about 18 chain atoms;
wherein $R^1$ has the structure of a side group of a proteinogenic amino acid and $R^2$ is —H;
wherein Z is a fragment of a perfume raw material,
wherein each J is $C(R^6)_2$,
wherein each $R^6$ is independently selected from H or a monovalent moiety with a molecular weight between 14 and 990 Da,
with the proviso that a first $R^6$ and a second $R^6$ can optionally be taken together, where feasible, as a divalent substituent, and
wherein at least one of the following is true:
(a) at least one of Q and an $R^6$, if present, comprises at least five, chain atoms, and/or
(b) an $R^6$ is present, and the sum of the number of chain atoms, in Q and the $R^6$ is at least eight;
wherein the treatment composition is a consumer product selected from the group consisting of a fabric care composition, a hard surface cleaner composition, a dish care composition, a hair care composition, a body cleansing composition, or a mixture thereof.

2. The treatment composition according to claim 1, wherein no $R^6$ group comprises more than 4 chain atoms.

3. The treatment composition according to claim 1, wherein the side chain is a side chain of a proteinogenic amino acid selected from the group consisting of alanine, glycine, valine, phenylalanine, leucine, isoleucine, or combinations thereof.

4. The treatment composition according to claim 1, wherein the fragment of a perfume raw material comprises an aldehyde moiety.

5. The treatment composition according to claim 1, wherein the fragment of a perfume raw material is selected from the group consisting of: methyl nonyl acetaldehyde: benzaldehyde; floralozone; isocyclocitral; triplal (ligustral); precylcemone B; lilial; decyl aldehyde; undecylenic aldehyde; cyclamen homoaldehyde; cyclamen aldehyde; dupical; oncidal; adoxal; melonal; calypsone; anisic aldehyde; heliotropin; cuminic aldehyde; scentenal; 3,6-dimethylcyclohex-3-ene-1-carbaldehyde; satinaldehyde; canthoxal; vanillin; ethyl vanillin; cinnamic aldehyde; cis-4-decenal; trans-4-decenal; cis-7-decenal; undecylenic aldehyde; trans-2-hexenal; trans-2-octenal; 2-undecenal; 2,4-dodecadeienal; cis-4-heptenal; Florydral; butyl cinnamaldehyde; limonelal; amyl cinnamaldehyde; hexyl cinnamaldehyde; citronellal; citral; cis-3-hexen-1-al; nerolione; 4-(4-methoxyphenyl)butan-2-one; 1-naphthalen-2-ylethanone; nectaryl; trimofix O; fleuramone; delta-damascone; beta-damascone; alpha-damascone; methyl ionone; 2-hexylcyclopent-2-en-1-one; galbascone; and mixtures thereof.

6. The treatment composition according to claim 1, wherein the adjunct ingredient comprises one or more of the following: surfactants, conditioning actives, deposition aids, rheology modifiers or structurants, bleach systems, antioxidants, stabilizers, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, silicones, hueing agents, aesthetic dyes, neat perfume, perfume delivery systems, structure elasticizing agents, carriers, hydrotropes, processing aids, anti-agglomeration agents, coatings, formaldehyde scavengers, and/or pigments.

7. The treatment composition according to claim 1, wherein the adjunct ingredient comprises a conditioning active.

8. The treatment composition according to claim 1, wherein the treatment composition is in the form of a liquid composition, a granular composition, a hydrocolloid, a single-compartment pouch, a multi-compartment pouch, a dissolvable sheet, a pastille or bead, a fibrous article, a tablet, a stick, a bar, a flake, a foam or mousse, a non-woven sheet, or a mixture thereof.

9. The treatment composition according to claim 1, wherein the pro-benefit-agent compound is present in the treatment composition at a level of from about 0.001% to about 30%, by weight of the treatment composition.

10. A method of treating an article or a surface, wherein the method comprises treating the article or surface with a treatment composition according to claim 1, optionally in the presence of water.

* * * * *